United States Patent [19]

Campion et al.

[11] Patent Number: 5,240,958
[45] Date of Patent: Aug. 31, 1993

[54] HYDROXAMIC ACID BASED COLLAGENASE INHIBITORS

[75] Inventors: Colin Campion; Alan H. Davidson, both of Oxon; Jonathan P. Dickens, Buckinghamshire; Michael J. Crimmin, Ascot, all of England

[73] Assignee: British Bio-Technology Limited, Oxford, England

[21] Appl. No.: 689,848

[22] PCT Filed: Nov. 23, 1989

[86] PCT No.: PCT/GB89/01399
§ 371 Date: Jul. 8, 1991
§ 102(e) Date: Jul. 8, 1991

[87] PCT Pub. No.: WO90/05719
PCT Pub. Date: May 31, 1990

[30] Foreign Application Priority Data

Nov. 23, 1988 [GB] United Kingdom ............ 8827305

[51] Int. Cl.$^5$ .................. A61K 31/38; C07D 333/34
[52] U.S. Cl. ............................ 514/445; 549/65; 548/465; 548/467; 548/315.1; 514/397; 514/414; 514/575; 562/622; 558/254
[58] Field of Search ........... 514/575, 415, 562, 397, 514/414; 562/622, 131, 432, 562, 430, 426, 431, 432, 563, 505, 506, 556, 557, 430; 558/254; 549/65; 548/315.1, 465, 467

[56] References Cited

U.S. PATENT DOCUMENTS

| | | | |
|---|---|---|---|
| 4,105,789 | 8/1978 | Ondetti et al. ............ | 424/309 |
| 4,496,540 | 1/1985 | Kim ........................ | 514/19 |
| 4,599,361 | 7/1986 | Dickens et al. .......... | 514/575 |
| 4,996,358 | 2/1991 | Handa et al. ............. | 562/621 |

FOREIGN PATENT DOCUMENTS

| | | |
|---|---|---|
| 0012401A1 | 6/1980 | European Pat. Off. |
| 0214639A2 | 3/1987 | European Pat. Off. |
| 0236872A2 | 9/1987 | European Pat. Off. |
| 0274453A2 | 7/1988 | European Pat. Off. |

OTHER PUBLICATIONS

J. March, "Advanced Organic Chemistry" 3rd ed., pp. 370-371, John Wiley & Sons, New York (1985).
Wooley et al., Arthritis and Rheumatism, 20: (No. 6): 1231-1239 (1977).
Cawston and Barrett, Anal. Biochem. 99:340-345 (1979).
Cawston et al., Biochem. J. 195: 159-165 (1981).
Cawston and Murphy, Methods in Enzymology, 80:711-722 (1981).

*Primary Examiner*—Mark Russell
*Attorney, Agent, or Firm*—Allegretti & Witcoff, Ltd.

[57] ABSTRACT

Compounds of general formula I:

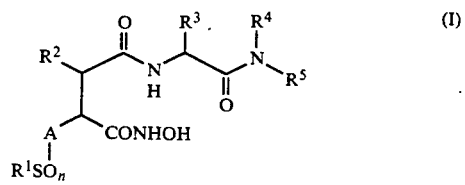

wherein:

$R^1$ represents a $C_1$-$C_6$ alkyl, phenyl, thiophenyl, substituted phenyl, phenyl($C_1$-$C_6$)alkyl, heterocyclyl, ($C_1$-$C_6$)alkylcarbonyl phenacyl or substituted phenacyl group; or, when n=0, $R^1$ represents $SR^x$, wherein $R^x$ represents a group:

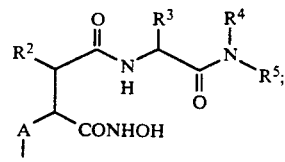

$R^2$ represents a hydrogen atom or a $C_1$-$C_6$ alkyl, $C_1$-$C_6$ alkenyl, phenyl ($C_1$-$C_6$) alkyl, cycloalkyl($C_1$-$C_6$)alkyl or cycloalkenyl($C_1$-$C_6$)alkyl group;
$R^3$ represents an amino acid residue with R or S ste-
(Abstract continued on next page.)

reochemistry or a $C_1$-$C_6$ alkyl, benzyl, ($C_1$-$C_6$ alkoxy)benzyl or benzyloxy($C_1$-$C_6$ alkyl) group;

$R^4$ represents a hydrogen atom or a $C_1$-$C_6$ alkyl group;

$R^5$ represents a hydrogen atom or a methyl group;

n is an integer having the value 0, 1 or 2; and

A represents a $C_1$-$C_6$ hydrocarbon chain, optionaly substituted with one or more $C_1$-$C_6$ alkyl, phenyl or substituted phenyl groups;

and their salts and N-oxides are collagenase inhibitors are and useful in the management of disease involving tissue degradation and/or the promotion of wound healing. Diseases involving tissue degradation include arthropathy (particularly rheumatoid arthritis), inflammation, dermatological diseases, bone resorption diseases and tumour invasion.

11 Claims, No Drawings

HYDROXAMIC ACID BASED COLLAGENASE INHIBITORS

BACKGROUND OF THE INVENTION

I. Field of the Invention

This invention relates to pharmaceutically and veterinarily active compounds, which are derivatives of hydroxamic acid.

II. Description of the Prior Art

The compounds of the present invention act as inhibitors of metalloproteases involved in tissue degradation, such as collagenase, which initiates collagen breakdown, stromelysin (protoglycanase), gelatinase and collagenase (IV). There is evidence implicating collagenase as one of the key enzymes in the breakdown of articular cartilage and bone in rheumatoid arthritis (*Arthritis and Rheumatism,* 20, 1231–1239, 1977). Potent inhibitors of collagenase and other metalloproteases involved in tissue degradation are useful in the treatment of rheumatoid arthritis and related diseases in which collagenolytic activity is important. Inhibitors of metalloproteases of this type can therefore be used in treating or preventing conditions which involve tissue breakdown; they are therefore useful in the treatment of arthropathy, dermatological conditions, bone resorption, inflammatory diseases and tumour invasion and in thepromotion of wound healing. Specifically, compounds of the present invention may be useful in the treatment of osteopenias such as osteoporosis, rheumatoid arthritis, osteoarthritis, periodontitis, gingivitis, corneal ulceration and tumour invasion.

A number of small peptide like compounds which inhibit metalloproteases have been described. Perhaps the most notable of these are those relating to the angiotensin converting enzyme (ACE) where such agents act to block the conversion of the decapeptide angiotensin I to angiotensin II a potent pressor substance. Compounds of this type are described in EP-A-0012401.

Certain hydroxamic acids have been suggested as collagenase inhibitors as in U.S. Pat. No. 4,599,361 and EP-A-0236872. Other hydroxamic acids have been prepared as ACE inhibitors, for example in U.S. Pat. No. 4,105,789, while still others have been described as enkephalinase inhibitors as in U.S. Pat. No. 4,496,540.

EP-A-0012401 discloses antihypertensive compounds of the formula:

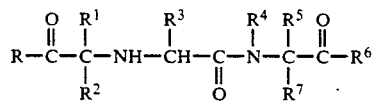

wherein

R and $R^6$ are the same or different and are hydroxy, alkoxy, alkenoxy, dialkylamino alkoxy, acylamino alkoxy, acyloxy alkoxy, aryloxy, alkyloxy, substituted aryloxy or substituted aralkoxy wherein the substituent is methyl, halo, or methoxy, amino, alkylamino, dialkylamino, aralkylamino or hydroxyamino;

$R^1$ is hydrogen, alkyl of from 1 to 20 carbon atoms, including branched, cyclic and unsaturated alkyl groups;

substituted alkyl wherein the substituent is halo, hydroxy, alkoxy, aryloxy amino, alkylamino, dialkylamino, acrylamino, arylamino, guanidino, imidazolyl, indolyl, mercapto, alkylthio, arylthio, carboxy, carboxamido, carbalkoxy, phenyl, substituted phenyl wherein the substituent is alkyl, alkoxy or halo; aralkyl or heteroaralkyl, aralkenyl or heteroaralkenyl, substituted aralkyl, substituted heteroaralkyl, substituted aralkenyl or substituted hetereoaralkenyl, wherein the substituent is halor or dihalo, alkyl, hydroxy, alkoxy, amino, aminomethyl, acrylamino, dialkylamino, alkylamino, carboxyl, haloalkyl, cyano or sulphonamido, aralkyl or hetereoaralkyl substituted on the alkyl portion by amino or acylamino;

$R^2$ and $R^7$ are hydrogen or alkyl;

$R^3$ is hydrogen, alkyl, phenylalkyl, aminomethylphenylalkyl, hydroxyphenylalkyl, hydroxyalkyl, acetylaminoalkyl, acylaminoalkyl, acylaminoalkyl aminoalkyl, dimethylaminoalkyl, haloalkyl, guanidinoalkyl, imidazolylalkyl, indolylalkyl, mercaptoalkyl and alkylthioalkyl;

$R^4$ is hydrogen or alkyl;

$R^5$ is hydrogen, alkyl, phenyl, phenylalkyl, hydroxyphenylalkyl, hydroxyalkyl, aminoalkyl, guanidinoalkyl, imidazolylalkyl, indolylalkyl, mercaptoalkyl or alkylthioalkyl;

$R^4$ and $R^5$ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with hydroxy, alkoxy or alkyl and the pharmaceutically acceptable salts thereof.

U.S. Pat. No. 4,599,361 discloses compounds of the formula:

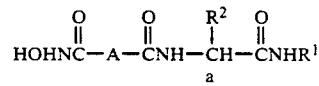

wherein $R^1$ is $C_1$–$C_6$ alkyl;

$R^2$ is $C_1$–$C_6$ alkyl, benzyl, benzyloxybenzyl, ($C_1$–$C_6$ alkoxy)benzyl or benzyloxy($C_1$–$C_6$ alkyl);

a is a chiral centre with optional R or S stereochemistry;

A is a

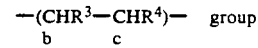

or a —$(CR^3{=}CR^4)$— group wherein b and c are chiral centres with optional R or S stereochemistry;

$R^3$ is hydrogen, $C_1$–$C_6$ alkyl, phenyl or phenyl($C_1$–$C_6$ alkyl) and $R^4$ is hydrogen, $C_1$–$C_6$ alkyl, phenyl(-$C_1$–$C_6$ alkyl), cycloalkyl or cycloalkyl($C_1$–$C_6$ alkyl).

EP-A-0236872 discloses generically compounds of the formula

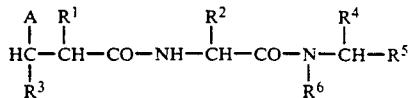

wherein

A represents a group of the formula HN(OH)—CO— or HCO—N(OH)—;

$R^1$ represents a $C_2$-$C_5$ alkyl group;

$R^2$ represents the characterising group of a natural alpha-amino acid in which the functional group can be protected, amino groups may be acylated and carboxyl groups can be amidated, with the proviso that $R^2$ can not represent hydrogen or a methyl group;

$R^3$ represents hydrogen or an amino, hydroxy, mercapto, $C_1$-$C_6$ alkyl, $C_1$-$C_6$ alkoxy, $C_1$-$C_6$ acylamino, $C_1$-$C_6$-alkylthio, aryl-($C_1$-$C_6$ alkyl)-, amino-($C_1$-$C_6$-alkyl)-, hydroxy($C_1$-$C_6$-alkyl)-, mercapto($C_1$-$C_6$ alkyl) or carboxy($C_1$-$C_6$ alkyl) group, wherein the amino, hydroxy, mercapto or carboxyl groups can be protected and the amino groups may be acylated or the carboxyl groups may be amidated;

$R^4$ represents hydrogen or a methyl group;

$R^5$ represents hydrogen or a $C_1$-$C_6$ acyl, $C_1$-$C_6$ alkoxy-$C_1$-$C_6$ alkyl, di($C_1$-$C_6$-alkoxy)methylene, carboxy, ($C_1$-$C_6$ alkyl)carbinyl, ($C_1$-$C_6$ alkoxy)carbinyl, arylmethoxy carbinyl, ($C_1$-$C_6$ alkyl)amino carbinyl or arylamino carbinyl group; and $R^6$ represents hydroxy or a methylene group; or $R^2$ and $R^4$ together represent a group-$(CH_2)_n$—, wherein n represents a number from 4 to 11; or $R^4$ and $R^5$ together represent a trimethylene group;

and pharmaceutically acceptable salts of such compounds, which are acid or basic.

U.S. Pat. No. 4,105,789 generically discloses compounds which have the general formula

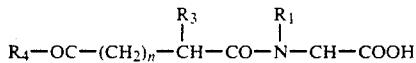

and salts thereof, wherein $R_1$ is hydrogen, lower alkyl, phenyl lower alkylene, hydroxy-lower alkylene, hydroxyphenyl lower alkylene, amino-lower alkylene, guanidine lower alkylene, mercapto-lower alkylene, lower alkyl-mercapto-lower alkylene, imidazolyl lower alkylene, indolyl-lower alkylene or carbamoyl lower alkylene;

$R_2$ is hydrogen or lower alkyl;

$R_3$ is lower alkyl or phenyl lower alkylene;

$R_4$ is hydroxy, lower alkoxy or hydroxyamino; and n is 1 or 2.

U.S. Pat. No. 4,496,540 discloses compounds of the general formula

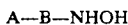

wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine; and pharmaceutically acceptable salts thereof.

It would however be desirable to improve on the solubility of known collagenase inhibitors and/or stomelysin inhibitors (whether as the free base or the salt) and, furthermore, increases in activity have also been sought. It is not a simple matter, however, to predict what variations in known compounds would be desirable to increase or even retain activity; certain modifications of known hydroxamic acid derivatives have been found to lead to loss of activity.

SUMMARY OF THE INVENTION

According to a first aspect of the invention, there is provided a compound of general formula I:

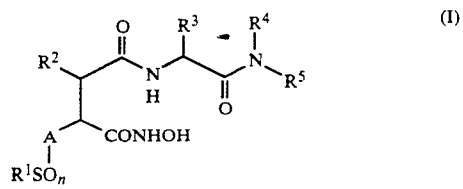

wherein:

$R^1$ represents a hydrogen atom $C_1$-$C_6$ alkyl, phenyl, thienyl, substituted phenyl, phenyl($C_1$-$C_6$)alkyl, heterocyclyl, ($C_1$-$C_6$)alkylcarbonyl, phenacyl or substituted phenacyl group; or, when n=O, $R^1$ represents $SR^x$, wherein $R^x$ represents a group:

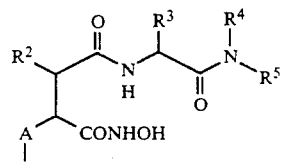

$R^2$ represents a hydrogen atom or a $C_1$-$C_6$ alkyl, $C_1$-$C_6$ alkenyl, phenyl($C_1$-$C_6$) alkyl, cycloalkyl(-$C_1$-$C_6$)alkyl or cycloalkenyl($C_1$-$C_6$)alkyl group;

$R^3$ represents an amino acid side chain or a $C_1$-$C_6$ alkyl, benzyl, ($C_1$-$C_6$ alkoxy) benzyl, benzyloxy(C-1-$C_6$ alkyl) or benzyloxybenzyl group;

$R^4$ represents a hydrogen atom or a $C_1$-$C_6$ alkyl group;

$R^5$ represents a hydrogen atom or a methyl group;

n is an integer having the value 0, 1 or 2; and

A represents a $C_1$-$C_6$ hydrocarbon chain, optionaly substituted with one or more $C_1$-$C_6$ alkyl, phenyl or substituted phenyl groups;

or a salt thereof.

DETAILED DESCRIPTION OF THE INVENTION

Hereafter in this specification, the term "compound" includes "salt" unless the context requires otherwise.

As used herein the term "$C_1$-$C_6$ alkyl" refers to a straight or branched chain alkyl moiety having from one to six carbon atoms, including for example, methyl, ethyl, propyl, isopropyl, butyl, t-butyl, pentyl and hexyl, and cognate terms (such as "$C^1$-$C^6$ alkoxy") are to be construed accordingly.

The term "$C_1$-$C_6$ alkenyl" refers to a straight or branched chain alkyl moiety having one to six carbons and having in addition one double bond, of either E or Z stereochemistry where applicable. This term would include, for example, an alpha, beta-unsaturated methylene group, vinyl, 1-propenyl, 1- and 2-butenyl and 2-methyl-2-propenyl.

The term "cycloalkyl" refers to a saturated alicyclic moiety having from 3 to 8 carbon atoms and includes for example, cyclopropyl, cyclobutyl, cyclopentyl and cyclohexyl.

The term "cycloalkenyl" refers to an unsaturated alicycle having from 3 to 8 carbon atoms and includes cyclopropenyl, cyclobutenyl and cyclopentenyl, cyclohexenyl.

The term "substituted", as applied to a phenyl or other aromatic ring, means substituted with up to four substituents each of which independently may be $C_1$-$C_6$ alkyl, $C_1$-$C_6$ alkoxy, hydroxy, thiol, $C_1$-$C_6$ alkylthiol, amino, halo (including fluoro, chloro, bromo and iodo), triflouromethyl or nitro.

The term "amino acid side chain" means a characteristic side chain attached to the —$CH(NH_2)(COOH)$ moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

The term "hydrocarbon chain" includes alkylene, alkenylene and alkynylene chains of from 1 to 6 carbon atoms. Preferably the carbon atom of the hydrocarbon chain nearest to the hydroxamic acid group is a methylene carbon atom.

There are several chiral centres in the compounds according to the invention because of the presence of asymmetric carbon atoms. The presence of several asymmetreic carbon atoms gives rise to a number of diastereomers with the appropriate R or S stereochemistry at each chiral centre. General formula I and, where apprpriate, all other formulae in this specification are to be understood to include all such stereoisomers and mixtures (for example racemic mixtures) thereof. Compounds in which the chiral centre adjacent the substituent $R^3$ has S stereochemistry and/or the chiral centre adjacent the substituent $R^2$ has R stereochemistry are preferred.

Further or other preferred compounds include those in which, independently or in any combination:

$R^1$ represents a hydrogen atom or a $C_1$-$C_4$ alkyl, phenyl, thienyl, benzyl, acetyl or benzoyl group;

$R^2$ represents a $C_3$-$C_6$ alkyl (for example isobutyl) group;

$R^3$ represents a benzyl or 4-($C_1$-$C_6$)alkoxyphenylmethyl or benzyloxybenzyl group;

$R^4$ represents a $C_1$-$C_4$ alkyl (for example methyl) group; and $R^5$ represents a hydrogen atom.

Particularly preferred compounds include:

1. [4-(Hydroxyamino)-2R-isobutyl-3S-(phenylthiomethyl)-succinyl]-L-phenylalanine-N-methylamide,
2. [4-(N-Hydroxyamino)-2R-isobutyl-3S-(thienylthiomethyl) succinyl]-L-phenylalanine-N-methylamide,
3. [4-(N-Hydroxyamino)-2R-isobutyl-3S-(benzylthiomethyl)succinyl]-L-phenylalanine-N-methylamide,
4. [4-(N-Hydroxyamino)-2R-isobutyl-3S-(acetylthiomethyl)succinyl]-L-phenylalanine-N-methylamide and
5. [4-(N-Hydroxyamino)-2R-isobutyl-3S-(mercaptomethyl)succinyl]-L-phenylalanine-N-methylamide
6. [4-(N-Hydroxyamino)-2R-isobutyl-3S-(benzoylthiomethyl)succinyl]-L-phenylalanine-N-methylamide
7. [4-(N-Hydroxyamino)-2R-isobutyl-3S-(pivaloylthiomethyl)succinyl]-L-phenylalanine-N-methylamide
8. [4-(N-Hydroxyamino)-2R-isobutyl-3S-(phenylthiomethyl)succinyl]-L-phenylalanine-N-methylamide sodium salt
9. [4-(N-Hydroxyamino)-2R-isobutyl-3S-(4-methoxyphenyl-thiomethyl)succinyl]-L-phenylalanine-N-methylamide
10. [4-(N-Hydroxyamino)-2R-isobutyl-3S-(4-hydroxyphenylthiomethyl)succinyl]-L-phenylalanine-N-methylamide
11. [4-(N-Hydroxyamino)-2R-isobutyl-3S-(2-thiophenethiomethyl)succinyl]-L-phenylalanine-N-methylamide sodium salt
12. [4-(N-Hydroxyamino)-2R-isobutyl-3S-(4-methoxyphenylthiomethyl)succinyl]-L-phenylalanine-N-methylamide sodium salt
13. [4-(N-Hydroxyamino)-2R-isobutyl-3S-(4-tert-butylphenylthiomethyl)succinyl]-L-phenylalanine-N-methylamide
14. [4-(N-Hydroxyamino)-2R-isobutyl-3S-(2,4-dimethylphenylthiomethyl)succinyl]-L-phenylalanine-N-methylamide
15. bis-S,S'-{[4(N-Hydroxyamino-2R-isobutyl-3S-(thiomethyl)succinyl]-L-phenylalanine-N-methylamide} disulphide
16. [4-(N-Hydroxyamino)-2R-isobutyl-3S-(3-bromophenylthio-methyl)succinyl]-L-phenylalanine-N-methylamide
17. [4-(N-Hydroxyamino)-2R-isobutyl-3S-(3-chlorophenylthiomethyl)succinyl]-L-phenylalanine-N-methylamide
18. [4-(N-Hydroxyamino)-2R-isobutyl-3S-(3-methylphenylthiomethyl)succinyl]-L-phenylalanine-N-methylamide
19. [4-(N-Hydroxyamino)-2R-isobutyl-3S-(4-(N-acetyl)aminophenylthiomethyl)succinyl]-L-phenylalanine-N-methylamide
20. [4-(N-Hydroxyamino)-2R-isobutyl-3S-phenylsulphinylmethylsuccinyl]-L-phenylalanine-N-methylamide
21. [4-(N-Hydroxyamino)-2R-isobutyl-3S-phenylsulphonylmethylsuccinyl]-L-phenylalanine-N-methylamide
22. [4-(N-Hydroxyamino)-2R-isobutyl-3S-thienylsulphinylmethyl-succinyl]-L-phenylalanine-N-methylamide
23. [4-(N-Hydroxyamino)-2R-isobutyl-3S-thienylsulphonylmethyl-succinyl]-L-phenylalanine-N-methylamide
24. [4-(N-Hydroxyamino)-2R-isobutyl-3S-phenylsulphonylmethyl-succinyl]-L-phenylalanine-N-methylamide sodium salt
25. [4-(N-Hydroxyamino)-2R-isobutyl-3S-(4-(isobutyloxycarbonylamino)phenyl)thiomethyl-succinyl]-L-phenylalanine-N-methylamide
26. [4-(N-Hydroxyamino)-2R-isobutyl-3S-(4-(N-methyl-N-(tert-butoxycarbonyl)-glycylamino)phenyl)thiomethylsuccinyl]-L-phenylalanine-N-methylamide and, where appropriate, their salts. Compounds 2 and 5 are especially preferred and compound 2 is the most preferred, because of its good collagenase-inhibiting and protoglycanase-inhibiting activities.

Compounds of general formula 1 may be prepared by any suitable method known in the art and/or by the following process, which itself forms part of the invention.

According to a second aspect of the invention, there is provided a process for preparing a compound of general formula I as defined above, the process comprising:

(a) deprotecting a compound of general formula II

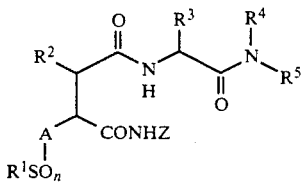

wherein: $R^1$, $R^2$, $R^3$, $R^4$, $R^5$, A and n are as defined in general formula I and Z represents a protective group such as a benzyl group; or (b) reacting a compound of general formula III

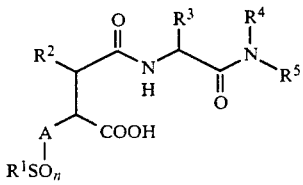

wherein: $R^1$, $R^2$, $R^3$, $R^4$, $R^5$, A and n are as defined in general formula I, with hydroxylamine or a salt thereof; or (c) reacting a compound of general formula VIA

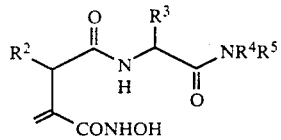

wherein $R^2$, $R^3$, $R^4$ and $R^5$ are as defined in general formula I, either with a thiol of the general formula $R^1S$, wherein $R^1$ is as defined in general formula I to give a compound of general formula I in which A represents a methylene group and n is 0, or with a cuprate of the general formula $(R^1S—A^1)_2CuLi$, wherein $R^1$ is as defined in general formula I and $A^1$ is such that $—A^1—CH_2—$ is identical to $—A—$, as defined in general formula I.

(d) optionally after step (a), step (b) or step (c) converting a compound of general formula I into another compound of general formula I.

Compounds of general formula I which are sulphoxides or sulphones can be derived from thiol compounds of general formula I by oxidation. Alternatively, thiols of general formula II or III may be oxidised. Compounds of general formula I which are disulphides (i.e. compounds wherein $R^1$ represents $SR^x$) may be derived from thiol esters of general formula I by milk oxidation, for example in air.

A compound of general formula II may be prepared from a compound of general formula III by reaction with an O-protected (such as benzyl) hydroxylamine. A compound of general formula III may be prepared by desterification (such as hydrolysis) of an ester of the general formula IV

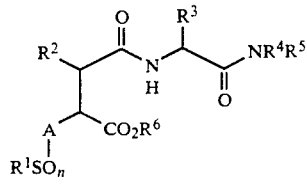

wherein: $R^1$, $R^2$, $R^3$, $R^4$, $R^5$, A and n are as defined in general formula I and $R^6$ represents $C_1-C_6$ alkyl, phenyl $C_1-C_6$ alkyl or substituted phenyl $C_1-C_6$ alkyl.

A compound of general formula IV can be prepared from an ester of general formula V or an acid of general formula VI

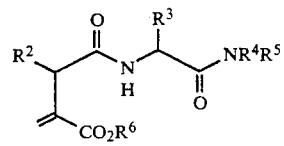

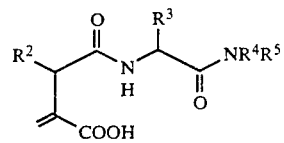

wherein: $R^2$, $R^3$, $R^4$ and $R^5$ are as defined in general formula I and $R^6$ represents $C_1-C_6$ alkyl, phenyl $C_1-C_6$ alkyl or substituted phenyl $C_1-C_6$ alkyl by reaction with a thiol $R^1SH$, wherein $R^1$ is as defined in general formula I, to give compounds wherein A represents a methylene group, or by reaction with a cuprate of the general formula $(R^1S—A^1)_2CuLi$, wherein $R^1$ is as defined in general formula I and $A^1$ is such that $—A^1—CH_2—$ is identical to $—A—$, as defined in general formula I.

Esters of general formula V can be prepared by esterifying acids of general formula VI with an appropriate alcohol $R^6OH$ or other esterifying agent.

Compounds of general formula VIA can be prepared by reacting compounds of general formula VI with hydroxylamine or a salt thereof.

An acid of general formula VI can be prepared by reacting a malonic acid derivative of general formula VII

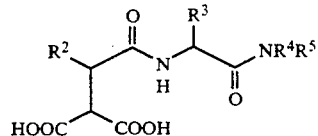

wherein: $R^2$, $R^3$, $R^4$ and $R^5$ are as defined in general formula I with formaldehyde in the presence of pyridine.

An acid of general formula VII can in turn be prepared by desterifying (for example hydrolysing) a compound of general formula VIII

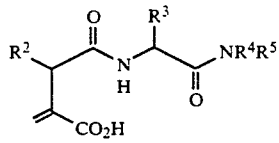

(VIII)

wherein: $R^2$, $R^3$, $R^4$ and $R^5$ are as defined in general formula I and $R^6$ represents $C_1$-$C_6$ alkyl, phenyl $C_1$-$C_6$ alkyl or substituted phenyl $C_1$-$C_6$ alkyl.

A compound of general formula VIII can be prepared by reacting a compound of general formula IX with a compound of general formula X

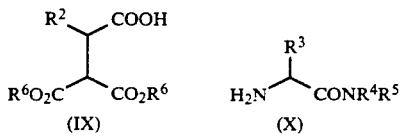

wherein: $R^2$, $R^3$, $R^4$ and $R^5$ are as defined in general formula I and $R^6$ represents $C_1$-$C_6$ alkyl, phenyl $C_1$-$C_6$ alkyl or substituted phenyl $C_1$-$C_6$ alkyl.

The starting materials and other reagents are either available commercially or can be synthesised by simple chemical procedures.

For example, a substituted acid of general formula IX may be prepared by reacting an ester of the general formula XI

wherein Y represents halo and $R^5$ is as defined above and $R^2$ and $R^6$ as defined above, with a malonate derivative of the general formula XII

wherein $R^6$ is as defined above with the proviso that when $R^6$ is aromatic in general formula XI it is aliphatic in general formula XII or vice versa, and selectively de-esterifying.

Compounds of general formula XI can simply be derived from amino acids, which can be obtained in enantiomerically pure form, enabling a choice of optically active compounds of general formula I to be prepared.

Compounds of general formulae II and III are valuable intermediates in the preparation of compounds of general formula I. According to a third aspect of the invention, there is therefore provided a compound of general formula II. According to a fourth aspect of the invention, there is provided a compound of general formula III.

As mentioned above, compounds of general formula I are useful in human or veterinary medicine as they are active inhibitors, of metalloproteases involved in tissue degradation.

According to a fifth aspect of the invention, there is provided a compound of general formula I for use in human or veterinary medicine, particularly in the management (by which is meant treatment of prophylaxis) of disease involving tissue. degradation, in particular rheumatoid arthritis, and/or in the promotion of wound healing.

According to a sixth aspect of the invention, there is provided the use of a compound of general formula I in the preparation of an agent for the management of disease involving tissue degradation, particularly rheumatoid arthritis, and/or in the promotion of wound healing. Compounds of general formula I can therefore be used in a method of treating disease involving tissue degradation, particularly rheumatoid arthritis, and/or in a method of promoting wound healing, the method in either case comprising administering to a human or animal patient an effective amount of a compound of general formula I.

The potency of compounds of general formula I to act as inhibitors of collagenase (a metalloprotease involved in tissue degradation) was determined by the procedure of Cawston and Barrett, (Anal. Biochem., 99, 340-345, 1979) and their potency to act as inhibitors of stromelysin was determined using the procedure of Cawston et al. (Biochem. J., 195, 159-165 19891), both of which techniques are to be described more fully in the examples and are incorporated by reference herein so far as the law allows.

According to a seventh aspect of the invention, there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptible carriers and/or. diluents and/or adjuvents and if desired other active ingredients.

According to an eighth aspect of the invention, there is provided a process for the preparation of a pharmaceutical or veterinary formulation in accordance with the seventh aspect, the process comprising admixing a compound of general formula I and a pharmaceutically and/or veterinarily acceptable carrier.

Compounds of general formula I may be formulated for administration by any route and would depend on the disease being treated. The compositions may be in the form of tablets, capsules, powders, granules, lozenges, liquid or gel preparations, such as oral, topical, or sterile parental solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers for example lactose, sugar, maize-starch, calcium phosphate, sorbitol or glycine; tabletting lubricant, for example magnesium sterate, talc, polyethylene glycol or silica; disintegrants, for example potato starch, or acceptable wetting agents such as sodium lauryl sulphate. The tablets may be coated according to methods well known in normal pharmaceutical practice Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain coventional additives such as suspending agents, for example sorbitol, syrup, methyl cellulose, glucose syrup, gelatin, hydrogenated edible fats; emulsifying agents, for example lecithin, sorbitan monooleate, or acacia; non-aqujeous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of general formula I. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin the drug may be made up into a cream, lotion or ointment. Cream or ointment formulations that may be used for the drug are conventional fomulations well known in the art, for example, as described in standard text books of pharmaceutics such as the British Pharmacopoeia.

For topical applications to the eye, the drug may be made up into a solution or suspension in a suitable sterile aqueous or non-aqueous vehicle. Additives, for instance buffers such as sodium metabisulphite or disodium edeate; preservatives including bactericidal and fungicidal agents, such as phenyl mercuric acetate or nitrate, benzalkonium chloride or chlorohexidine, and thickening agents such as hypromellose may also be included.

The dosage employed for the topical administration will, of course, depend on the size of the area being treated. For the eyes each dose will be typically in the range from 10 to 100 mg of the compound of general formula I.

The active ingredient may also be administered parenterally in a sterile medium. The drug depending on the vehicle and concentration used, can either be suspended or dissolved in the vehicle. Advantageously, adjuvants such as a local anasthetic, preservative and buffering agents can be dissolved in the vehicle.

For use in the treatment of rheumatoid arthritis the compounds of this invention can be administered by the oral route or by injection intra-articularly into the affected joint. The daily dosage for a 70 kg mammal will be in the range of 10 mgs to 1 gram of a compound of general formula I.

The following examples illustrate the invention, but are not intended to limit the scope in any way. The following abbreviations, have been used in the Examples:

DCC—Dicyclohexylcarbodiimide
DCM—Dichloromethane
DCU—Dicyclohexylurea
DIPE—Diisopropyl ether
DMF—N,N-dimethylformamide
HOBT—Hydroxybenztriazole
NMM—N-Methylmorpholine
TFA—Trifluoroacetic acid
THF—Tetrahydrofuran
WSCDI—N-(Dimethylaminoethyl)-N'-ethylcarbodiimide

EXAMPLE 1

[4-(N-Hydroxyamino)-2R-isobutyl-3S-(phenylthiomethyl)succinyl]-L-phenylalanine-N-methylamide

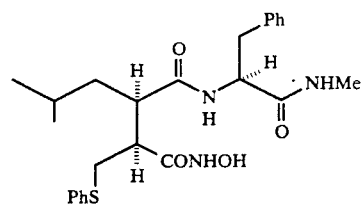

a) 2R-Bromo-5-methylpentanoic acid

D-Leucine (100 g, 0.76 mol) and potassium bromide (317.5 g, 2.67 mol) were dissolved in aqueous acid (150 ml concentrated sulphuric acid in 500 ml of water). The solution was cooled to −2° and sodium nitrite (69.6 g, 0.95 mol in water) was added over 1 h taking care to maintain the temperature between −1° and −2°. After addition was complete the mixture was kept at 0° for a further hour, then DCM was added and the mixture stirred for a few minutes. The layers were separated and the aqeous phase was washed with further portions of DCM (5×250 ml). The combined organic layers were dried over magnesium sulphate then the solvent removed to give the acid as a pale yellow oil (123.1 g, 0.63 mol, 83%).

$[alpha]_D= +38.0°$ (c=2, methanol).

$delta_H$ (250 MHz, CDCl$_3$) 4.29 (1H, t, J=6.5 Hz, BrCHCO$_2$H), 1.91 (2H, t, J=7 Hz, CHCH$_2$CH), 1.83 (1H, m, Me$_2$CH), and 0.94 (6H, 2xd, J=7 Hz, (CH$_3$)$_2$CH).

b) tert-Butyl 2R-Bromo-5-methylpentanoate

2R-Bromo-5-methylpentanoic acid (123 g, 0.63 mol) was dissolved in DCM (400 ml) and the solution cooled to −40° while isobutene was condensed in to roughly double the volume. Maintaining the temperature at −40° concentrated sulphuric acid (4 ml) was added dropwise. When the addition was complete the reaction was allowed to warm to room temperature overnight. The resultant solution was concentrated to half the volume by removing the solvent at reduced pressure, then the DCM was washed twice with an equal volume of 10% sodium bicarbonate solution. The organic layer was dried over magnesium sulphate and the solvent removed under reduced pressure to leave the title compound as a yellow oil (148.1 g, 0.59 mol, 94%). $[alpha]_D= +23.0°$ (c=2, methanol).

$delta_H$ (250 MHz, CDCl$_3$) 4.18 (1H, t, J=6 5 Hz, BrCHCO$_2$H), 1.89 (2H, m, CHCH$_2$CH), 1.78 (1H, m, Me$_2$CH), 1.49 (9H, s, (CH$_3$)$_3$C) and 0.94 (6H, 2xd, J=7 Hz, (CH$_3$)$_2$CH).

$delta_C$(63.9 MHz, CDCl$_3$) 167.0, 82.0, 46.3, 43.4, 27.6, 26.3, 22.2, and 21.6.

c) Benzyl (2-benzloxycarbonyl-3R-(tert-butoxycarbonyl)-5-methylhexanoate

Dibenzyl malonate (124.5 g, 0.44 mol) was taken up in dry DMF and potassium tert-butoxide (49.2 g, 0.44 mol) was added portionwise with stirring and cooling. When a homogeneous solution had formed it was cooled to 0° then tert-butyl-2R-bromo-5-methylpentanoate (110.1 g, 0.44 mol) in DMF (200 ml) was added dropwise over 1 h. When addition was complete the reaction was transfered to a cold room at <5° and left for 4 days. The reaction mixture was partitioned between ethyl acetate and saturated ammonium chloride then the aqueous layer extracted with further ethyl acetate (4×500 ml), drying and solvent removal left an oil (228 g) heavily contaminated with DMF. This oil was taken into ether (1 liter) and washed with brine (2×1l) then the organic layer dried (magnesium sulphate), solvent removed under reduced pressure to leave the desired material (179 g) contaminated with a small amount of dibenzyl malonate.

[alpha]$_D$ = +22.5° (c=2, methanol).

delta$_H$ (250 MHz, CDCl$_3$) 7.40–7.25 (10H, m, Aromatic H), 5.14 (4H, 2xABq, CH$_2$Ph), 3.77 (1H, d, J=10 Hz, BnO$_2$CCHCO$_2$Bn), 3.09 (1H, dt, J=10, 6 Hz, CH$_2$CHCO$_2$tBu), 1.50 (3H, m, CH$_2$+CHMe$_2$)1.41 (9H, s, C(CH$_3$)$_3$) and 0.88 (6H, 2xd, J=7 Hz).

d)
[4-Benzyloxy-3-benzyloxycarbonyl-2R-isobutylsuccinyl]-L-phenylalanine-N-methylamide Benzyl(2-benzyloxycarbonyl-5-methyl-3R-tert-butoxycarbonyl)-hexanoate (281.4 g, 0.56 mol) was taken up in 5% water in TFA (410 ml) and allowed to stand at 5° overnight. After this time the TFA was evaporated under reduced pressure then the residue partitioned between DCM (1l) and brine (200 ml). Solvent removal left an oil which crystallised on standing (230 g).

The crude acid from this reaction was dissolved in DMF (1l), then HOBT (95.3 g, 0.64 mol), NMM (64 g, 0.64 mol) and phenylalanine-N-methylamide (113.1 g, 0.64 mol) were added at room temperature. The mixture was cooled to 0° before dropwise addition of DCC (131.0 g, 0.64 mol) in THF (1l). This solution was stirred to room temperature over the weekend. The precipitated DCU was removed by filtration then the solvents were removed from the filtrate under reduced pressure to leave an oil. This oily residue was dissolved in ethyl acetate then washed with 10% citric acid, 10% sodium bicarbonate and saturated brine. The organic layer was dried (magnesium sulphate), filtered then the solvent removed under reduced pressure to give the title compound as an oil (400 g). This material was columned on silica using gradient elution (0–50% ethyl acetate in hexane) to remove impurities and separate a small amount of the minor diastereoisomer. The material from the column (195 g) was recrystallised from DIPE to give the title compound as a white crystalline solid (140.2 g, 0.25 mol, 47%)

m.p. 98°–99°.

Analysis calculated for C$_{33}$H$_{38}$N$_2$O$_6$: Requires: C 70.95, H 6.86, N 5.01. Found: C 70.56, H 6.89, N 5.06.

delta$_H$ (250 MHz, CDCl$_3$) 7.42–7.13 (15H ,m, Aromatic H), 6.58 (1H, d, J=7.7 Hz, CONH), 5.75 (1H, m, CONHMe), 5.20–5.05 (4H, m, OCH$_2$Ph), 4.50 (1H, dt, J=6.9, 7.7 Hz, CHCH$_2$Ph), 3.79 (1H, d, J=9.1 Hz, CH(CO$_2$Bn)), 3.15–2.91 (2H, m, CH$_2$Ph), 2.65 (3H, d, J=4.8 Hz, CONHCH$_3$), 1.52 (1H, m, CHCH$_2$CH), 1.32 (1H, m, CH(CH$_3$)), 1.05 (1H, m, CHCH$_2$CH), and 0.74 (6H, 2xd, J=6.5 Hz, CH(CH$_3$)$_2$)

e)
[4-Hydroxy-2R-isobutyl-3-ethenylsuccinyl]-L-phenylalanine-N-methylamide 4-Benzyloxy-3-benzyloxycarbonyl-2R-isobutylsuccinyl]-L-phenylalanine-N-methylamide (29.6 g, 53 mmol) was taken up in ethanol, ammonium formate (16.7 g, 265 mmol) added followed by 10% palladium on charcoal (6 g) as a slurry in isopropyl alcohol. After 30 minutes at room temperature the catalyst was removed by filtration, then washed with ethanol to give a solution of the crude diacid. To this was added piperidine (5.0 g) and the mixture stirred at room temperature for 15 minutes before addition of aqueous formaldehyde (40% solution, 25 ml). After 18 hours at room temperature the mixture was refluxed for 1 h. Solvents were removed under reduced pressure and the residue partitioned between ethyl acetate and citric acid. The acid layer was extracted with further portions of ethyl acetate (2×250 ml), the combined organic layers were extracted with potassium carbonate (3×200 ml). These base extracts were acidified to pH 4 and re-extracted with DCM then the organic layer dried over magnesium sulphate. Solvent removal under reduced pressure gave the desired product as a white solid (9.35 g, 27.0 mmol, 51%).

m.p. 149°–151° C.

delta$_H$ (250 MHz, CDCl$_3$) 8.37 (2H, d, J=9.0 Hz, CONH), 7.39 (1H, m, CONHMe), 7.27–7.06 (5H, m, Aromatic H), 6.40 (1H, s, CH$_2$CHCO$_2$H), 5.78 (1H, s, CH$_2$CHCO$_2$H), 4.93 (1H, q, J=7 Hz, CHCH$_2$Ph), 3.92 (1H, m, CH$_2$CHCONH), 2.95 (2H, m, CH$_2$Ph), 2.71 (3H, d, J=4.1 Hz, NHCH$_3$), 1.68 (1H, m), 1.45 (2H, m), and 0.86 (6H, 2xd, J=5.8 Hz, CH(CH$_3$)$_2$).

delta$_C$ (63.9 Hz, CDCl$_3$) 173.3, 172.8, 169.6, 139.1, 136.3, 129.2, 128.3, 127.0, 126.6, 54.4, 43.5, 41.4, 39.1, 26.2, 25.7, 22.5 and 22.4 f)
[4-Hydroxy-2R-isobutyl-3S-(phenylthiomethyl)succinyl]-L-phenylalanine-N-methylamide

[4-Hydroxy-2R-isobuty-3-ethenylsuccinyl]-L-phenylalanine-N-methylamide (15.1 g, 44 mmol) was dissolved in thiophenol (150 ml) and the mixture stirred in the dark under nitrogen at 60° for 2 days. Ether was added to the cooled reaction mixture and the precipitated product collected by filtration. The solid was washed with large volumes of ether and dried under vacuum to give the title compound (13.1 g, 28.7 mmol, 65%).

m.p. 199°–201° C.

Analysis calculated for C$_{25}$H$_{32}$N$_2$O$_4$S: Requires: C 65.76, H 7.06, N 6.14, S 7.02. Found: C 65.69, H 7.06, N 6.07, S 7.05.

delta$_H$ (250 MHz, D$_6$-DMSO) 8.40 (1H, d, J=9 Hz, CONH), 7.82 (1H, m, CONHMe), 7.35–7.10 (7H, m, Aromatic H), 7.04 (3H, m, Aromatic H), 4.62 (1H, m, CHCH$_2$Ph), 2.94 (1H, dd, J=14,5 Hz, CHCH$_2$Ph), 2.89 (1H, dd, J=14,9 Hz, CHCH$_2$Ph), 2.62 (3H, d, J=4.5 Hz, CONHCH$_3$), 2.41 (3H, m, 2xCH+CH$_2$SPh), 2.23 (1H, d, J=12 Hz, CH$_2$SPh), 1.43 (1H, m, CHCH$_2$CH), 1.30 (1H, bm, CH(CH$_3$)$_2$), 0.90 (1H, m, CHCH$_2$CH) and 0.78 (6H, 2xd, J=6.5 Hz, CH(CH$_3$)$_2$.

g)
[4-(N-Hydroxyamino)-2R-isobutyl-3S-(phenylthiomethyl) succinyl]-L-phenylalanine-N-methylamide

[4-Hydroxy-2R-isobutyl-3S-(phenylthiomethyl)succinyl]-L-phenylalanine-N-methylamide (16.8 g, 37 mmol) and HOBT (6.6 g, 44 mmol) were dissolved in DCM/DMF (4:1) and the mixture ccoled to 0° before adding WSCDI (8.5 g, 44 mmol) and NMM (4.5 g, 44 mmol). The mixture was stirred at 0° for 1 h to ensure complete formation of the activated ester. Hydroxylamine hydrochloride (3.8 g, 55 mmol) and NMM (5.6 g, 55 mmol) were dissolved in DMF then this mixture added dropwise to the cooled solution of the activated ester. After 1 h the reaction was poured into ether/water (1:1) whereupon the desired product precipitated as white crystals. These were collected by filtration, further washed with ether and water then dried under vacuum at 50°. This material was recrystallised from methanol/water (1:1) to remove a trace of the minor diastereomer (9.03 g, 19.2 mmol, 52%).

m.p. 227°-229° C.

[alpha]$_D$ = −88° (c = 10, methanol).

delta$_H$ (250 MHz, D$_6$-DMSO) 8.84 (1H, d, J = 1.5 Hz, NHOH), 8.35 (1H, d, J = 8.7 Hz, CONH), 7.87 (1H, m, CONHMe), 7.29-6.92 (11H, m, Aromatic H + NHOH), 4.6° (1H, m, CHCH$_2$Ph), 2.94 (1H, dd, J = 13.5,4.3, CHCH$_2$Ph), 2.77 (1H, dd, J = 13.5,10, CHCH$_2$Ph), 2.60 (3H, d,J = 4.6 Hz), 2.53 (1H, m), 2.41 (1H, m), 2.20 (1H, dd, J = 13.4,2.2 Hz, CH$_2$SPh), 2.09 (1H, dd, J = 13.4,2.4 Hz, CH$_2$SPh), 1.38 (2H, m, CHMe$_2$+CHCH$_2$CH), 0.88 (1H, m, CHCH$_2$CH), 0.82 (3H, d, J = 6.4 Hz, CH(CH$_3$)$_2$), and 0.74 (3H, d, J+6.4 Hz, CH(CH$_3$)$_2$).

delta$_C$ (63.9 MHz, D$_6$-DMSO) 172.9, 171.6, 166.3, 138.1, 136.7, 129.1, 128.9, 128.0, 127.3, 126.4, 125.2, 54.2, 46.4, 46.0, 37.7, 32.4, 25.6, 25.2, 24.2, and 21.7.

EXAMPLE 2

[4-(N-Hydroxyamino)-2R-isobutyl-3S-(thienylthiomethyl) succinyl]-L-phenylalanine-N-methylamide

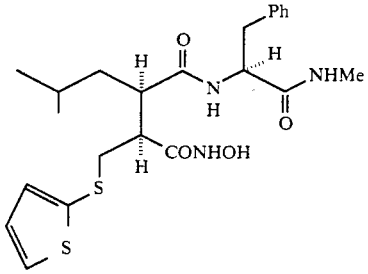

a) [4-N-Hydroxy-2R-isobutyl-3S-(thienylthiomethyl) succinyl]-L-phenylalanine-N-methylamide The title compound was prepared from [4-Hydroxy-2R-isobutyl-3-ethenylsuccinyl]-L-phenylalanine-N-methylamide (400 mg, 1.16 mmol) by the method described in example 1f, substituting thiophenethiol in the place of thiophenol to give a material (320 mg, 0.73 mmol, 63%) with the following characteristics.

m.p. 184°-186° C.

delta$_H$(250 MHz, D$_6$-DMSO) 8.29 (1H, d, J = 8.1 Hz, CONH), 7.84 (1H, m, CONHMe), 7.57 (1H, d, J = 5.1 Hz, Thiophene H), 5H, m, Aromatic H), 7.00 (2H, m, Thiophene H), 4.50 (1H, m, CHCH$_2$Ph), 2.91 (1H, m, CHCH$_2$Ph), 2.75 (1H, m, CHCH$_2$Ph), 2.56 (3H, d, J = 4.0 Hz, CONHCH$_3$), 2.34 (3H, m), 1.99 (1H, d, J = 9.3 Hz, CH$_2$SHet), 1.42 (1H, m, CHCH$_2$CH), 1.29 (1H, bm, CH(CH$_3$)$_2$), 0.87 (1H, m, CHCH$_2$CH), 0.79 (3H, d, J = 6.4 Hz, CH(CH$_3$)$_2$), and 0.72 (3H, d, J = 6.4 Hz, CH(CH$_3$)$_2$).

b) [4-(N-Hydroxyamino)-2R-isobutyl-3S-(thienylthiomethyl)succinyl]-L-phenylalanine-N-methylamide Prepared by the method described in example 1g to give material with the following characteristics m.p. 236°-238° C.

Analysis calculated for C$_{23}$H$_{30}$N$_2$O$_4$S$_2$: Requires: C 57.84, H 6.54, N 8.80. Found: C 57.64, H 6.48, N, 8.85.

delta$_H$ (250 MHz, D$_6$-DMSO) 8.80 (1H, s, CONHOH), 8.08 (1H, d, J = 8 Hz, CONH), 7.52 (1H, m, CONHMe), 7.32 (1H, dd, J = 4.6,2.9 Hz, Thiophene H), 7.17-6.95 (5H, m, Aromatic H), 6.89 (2H, m, Thiophene H), 4.46 (1H, m, CHCH$_2$Ph), 2.89 (1H, dd, J = 13.6,4.4 Hz, CHCH$_2$Ph), 2.72 (1H, dd, J = 13.6,10.5 Hz, CHCH$_2$Ph), 2.54 (3H, d, J = 4.3 Hz, CONHCH$_3$), 2.46 (1H, d, J = 12.1 Hz, CH$_2$S), 2.35 (1H, bt, J = 10.2 Hz), 2.14 (1H, bt, J = 10.2 Hz), 1.98 (1H, dd, J = 12.7,2.5 Hz, CHCH$_2$Ph), 1.35 (1H, bt, J = 11.4 Hz, CHCH$_2$CH), 1.22 (1H, bm, CH(CH$_3$)$_2$), 0.86 (1H, bt, J = 12.6 Hz, CHCH$_2$CH), 0.74 (3H, d, J = 6.3 Hz, CH(CH$_3$)$_2$), and 0.68 (3H, d, J = 6.4 Hz, CH(CH$_3$)$_2$).

delta$_C$ (63.9 MHz, D$_6$-DMSO) 172.5, 171.6, 166.1, 138.0, 133.8, 132.7, 129.4, 129.2, 128.1, 127.8, 126.5, 54.2, 46.2, 46.0, 38.5, 37.6, 25.8, 25.2, 24.2, and 21.7.

EXAMPLE 3

[4-(N-Hydroxyamino)-2R-isobutyl-3S-(benzylthiomethyl) succinyl]-L-phenylalanine-N-methylamide

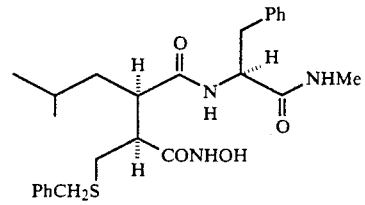

Prepared by the method described in example 1g to give material with the following characteristics Analysis calculated for C$_{27}$H$_{37}$N$_3$O$_5$S.0.5H$_2$O: Requires: C 61.81, H 7.30, N 8.00. Found: C 61.85, H 7.15, N 7.45.

delta$_H$ (250 MHz, D$_6$-DMSO) 8.40 (1H, s, CONHOH), 8.22 (1H, m, NHMe), 7.20 (5H, m, Aromatic H), 6.58 (4H, m), 4.10 (1H, m, CHCH$_2$Ph), 3.22 (3H, s, OCH$_3$), 3.04-2.45 (4H, m, 2xCH$_2$Ar), 2.42 (3H, d, J = 6 Hz, NHCH$_3$), 2.32-2.08 (4H, m), 0.78 (2H, m, CHCH$_2$CH), and 0.40-0.18 (7H, m, (CH$_3$)$_2$CH).

EXAMPLE 4

[4-(N-Hydroxyamino)-2R-isobutyl-3S-(acetylthiomethyl) succinyl]-L-phenylalanine-N-methylamide

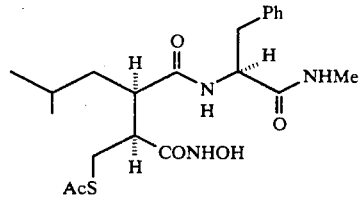

Prepared by the method described in example 1g to give material with the following characteristics m.p. 226°-227° C.

Analysis calculated for C$_{21}$H$_{31}$N$_3$O$_5$S.H$_2$O: Requires: C 55.37, H 7.30, N 9.22. Found: C 55.57, H 6.99, N 9.53.

delta$_H$ (250 MHz, D$_6$-DMSO) 8.84 (1H, s, NHOH), 8.36 (1H, d, J = 8 Hz, CONH), 7.80 (1H, d, J = 6 Hz, NHMe), 7.20 (% h, m, Aromatic H), 4.58 (1H, m, CHCH$_2$Ph), 3.16-2.62 (2H, m, CHCH$_2$Ph), 2.54 (3H, d, J = 4 Hz, NHCH$_3$), 2.22 (3H, s, CHCOS), 2.36-2.10

(4H, m, CHCHCH₂S), 1.36 (2H, m, CHCH₂CH), and 0.98–0.66 (7H, m, CH(CH₃)₂).

EXAMPLE 5

[4-(N-Hydroxyamino)-2R-isobutyl-3S-(mercaptomethyl) succinyl]-L-phenylalanine-N-methylamide

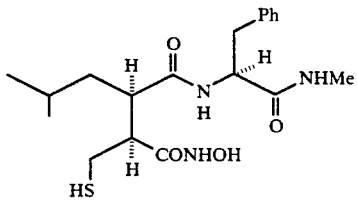

[4-(N-Hydroxyamino)-2R-isobutyl-3S-(acetylthiomethyl)succinyl]-L-phenylalanine-N-methylamide (30 mg, 0.06 mmol) was stirred in methanol (3 ml) with methylamine (1 ml methanolic solution) at room temperature. After 30 minutes the crystalline product (20 mg, 0.05 mmol, 74%) was filtered off and dried.

m.p. 234° C.

Analysis calculated for C₁₉H₃₉N₃O₄S.1.5H₂O: Requires: C 54.10, H 7.63, N 9.94, S 7.60. Found: C 54.28, H 7.16, N 10.43, S 7.80.

delta$_H$ (250 MHz, D₆-DMSO) 8.28 (1H, d, J=9 Hz, NHOH), 7.80 (1H, m, NHMe), 7.22 (5H, m, Aromatic H), 4.60 (1H, m, CHCH₂Ph), 3.08–2.56 (2H, m, CHCH₂Ph), 2.50 (3H, d, J=4 Hz, NHCH₃), 2.40–2.02 (4H, m, CHCHCH₂SH), 1.44–1.22 (2H, m, CHCH₂CH) and 0.98–0.72 (7H, m, CH(CH₃)₂).

EXAMPLE 6

[4-(N-Hydroxyamino)-2R-isobutyl-3S-(benzoylthiomethyl)succinyl]-L-phenylalanine-N-methylamide

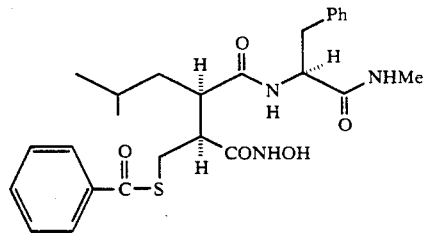

The title compound was prepared by the method described in Example 1g to give material with the following characteristics m.p. 227°–228°

Analysis calculated for C₂₁H₃₁N₃O₅S: Requires: C 62.50, H 6.66, N 8.4. Found: C 62.32, H 6.67, N 8.40.

delta$_H$(250 MHz, CDCl₃:D₆DMSO (1:1)) 8.82 (1H, s, NHOH), 8.25 (1H, d, J=8.4 Hz, NHOH), 7.87 (2H, dd, J=8.5, 1.1 Hz), 7.60 (2H, m, Ar-H and CONH), 7.50 (2H, t, J=8.2 Hz), 7.28 (2H, d, J=8.4 Hz), 7.16 (2H, t, J=7.2 Hz), 7.04 (1H, t, J=8.5 Hz), 4.65 (1H, m, CHCH₂Ph), 3.06 (1H, dd, J=14.1, 5.0Hz, CHCH₂Ph), 2.90 (1H, dd, J=13.9, 10 Hz, CHCH₂Ph), 2.73 (2H, m SCH₂Ph), 2.65 (3H, d, J=4.7 Hz, NHMe), 2.33 (1H, dt, J=11.0, 4.7 Hz), 1.51 (1H, t, J=7 Hz, CH₂CHMe₂), 1.24 (1H, m, CHMe₂), 0.97 (1H, t, J=7 Hz, CH₂CHMe₂), 0.84 (3H, d, J=6.5 Hz, CHMe₂) and 0.79 (3H, d, J=6.5 Hz, CHMe₂).

EXAMPLE 7

[4-(N-Hydroxyamino)-2R-isobutyl-3S-(pivaloylthiomethyl) succinyl]-L-phenylalanine-N-methylamide

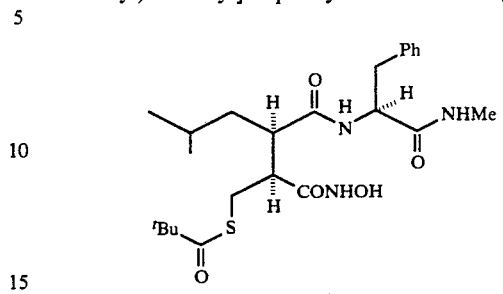

[4-Hydroxy-2R-isobutyl-3S-(pivaloylthiomethyl) succinyl]-L-phenylalanine-N-methylamide (0,8 g, 1.7 mmol) and HOBT (0.31 g, 2.1 mmol) were dissolved in 1:1 DCM/DMF and the mixture cooled to 0° C. before adding WSDCI (0.4 g, 2.1 mmol) and NMM (0.21 g, 2.1 mmol). The mixture was stirred at 0° C. for 1 h to ensure complete formation of the activated ester. Hydroxylamine hydrochloride (0.18 g, 2.6 mmol) and NMM (0.26 g, 2.6 mmol) were dissolved in DMF then this mixture was added dropwise to the cooled solution of the activated ester. After 1 h the reaction was poured into ether/water (1:1) whereupon the desired product precipitated as white crystals. These were collected by filtration, further washed with ether and water, then dried under vacuum at 50° C. This material was recrystallised from methanol/water (1:1) to remove a trace of the minor diastereomer (0.38 g, 0.7 mmol, 45%).

m.p. 225° C.

[alpha]$_D$ = −3.5° (c=2, methanol).

Analysis calculated for C₂₄H₃₉N₃O₅S.0.5 H₂O: Requires: C58.99, H7.84, N8.60. Found: C58.96, H7.63, N8.55.

delta$_H$ (250 MHz, D₆-DMSO) 8.81 (1H, s, J=1.5 Hz, NHOH), 8.30 (1H, d, J=8 Hz, CONH), 7.78 (1H, d, J=6 Hz, CONHMe), 7.27–7.03 (5H, m, aromatic H), 4.54 (1H, m, CHCH₂Ph), 2.94 (1H, dd, J=12,5 Hz, CHCH₂Ph), 2.79 (1H, dd, J=13,10 Hz, CHCH₂Ph) 2.56 (3H, d, J=4.5 Hz, NHCH₃), 2.44 (2H, m), 2.20 (1H, dd, J=13,3 Hz, CH₂S), 2.07 (1H, dt), 1.36 (2H, m), 1.13 (9H, s, C(CH₃)₃), 0.87 (1H, m, CH₂CH(CH₃)₂), 0.79 (3H, d, J=6 Hz, CH(CH₃)₂), and 0.74 (3H, d, J=6 Hz, CH(CH₃)₂).

delta$_C$(63.9 MHz, D₆-DMSO) 172.55, 171.59, 168.24, 138.03, 129.18, 128.00, 126.24, 54.21, 46.48, 45.84, 45.55, 37.61, 28.30, 27.13, 25.64, 25.25, 24.24, and 21.63.

EXAMPLE 8

[4-(N-Hydroxyamino)-2R-isobutyl-3S-(phenylthiomethyl) succinyl]-L-phenylalanine-N-methylamide sodium salt

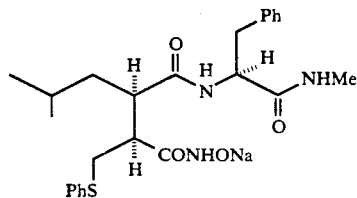

[4-(N-Hydroxyamino)-2R-isobutyl-3S-(phenylthiomethyl) succinyl]-L-phenylalanine-N-methylamide (0.2 g, 0.4 mmol) was dissolved in 20 ml of methanol and 1 eq of 0.1N NaOH(aq) added. The solvent was removed in vacuo and the residue dissolved in water and freeze-dried (0.21 g,0.4 mmol, 100%).

m.p. 184° C.

[alpha]$_D$= −7.7° (c=2, methanol).

delta$_H$ (250 MHz, D$_6$-DMSO) 8.62 (1H, s, J=1.5 Hz, NHO$\underline{H}$), 8.28 (1H, d, J=8 Hz, CON$\underline{H}$), 7.26–7.04 (10H, m, aromatic H), 4.43 (1H, m, C$\underline{H}$CH$_2$Ph), 3.00 (1H, dd, J=14,4 Hz, CHC$\underline{H}$Ph), 2.84 (1H, dd, J=14,10 Hz, CHC$\underline{H}_2$Ph), 2.55 (3H, d, J=4.5 Hz, NHC$\underline{H}_3$), 2.46 (3H, m), 2.21 (1H, m), 1.39 (1H, m), 1.14 (1H, m), 1.00 (1H,m), and 0.70 (6H, d , J=5.7 Hz)

EXAMPLE 9

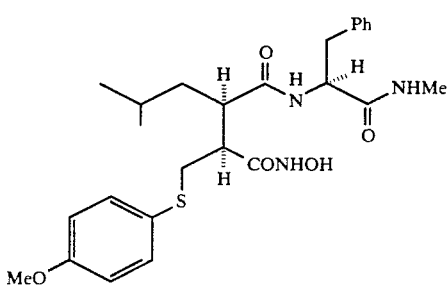

[4-(N-Hydroxyamino)-2R-isobutyl-3S-(4-methoxy-phenylthiomethyl) succinyl]-L-phenylalanine-N-methylamide[4-Hydroxy-2R-isobutyl-3S-(4-methoxy-phenylthiomethyl)succinyl]-L-phenylalanine-N-methylamide (0,5 g, 1 mmol) and HOBT (0.18 g, 1.2 mmol) were dissolved in 1:1 DCM/DMF and the mixture cooled to 0° C. before adding WSDCI (0.23 g, 1.2 mmol) and NMM (0.12 g, 1.2 mmol). The mixture was stirred at 0° C. for 1h to ensure complete formation of the activated ester. Hydroxylamine hydrochloride (0.1 g, 1.5 mmol) and NMM (0.15 g, 1.5 mmol) were dissolved in DMF then this mixture was added dropwise to the cooled solution of the activated ester. After 1 h the reaction was poured into ether/water (1:1) whereupon the desired product precipitated as white crystals. These were collected by filtration, further washed with ether and water, then dried under vacuum at 50° C. This material was recrystallised from methanol/water (1:1) to remove a trace of the minor diastereomer (0.36 g, 0.7 mmol, 72%).

m.p. 225° C.

[alpha]$_D$= +8° (c=0.5, methanol).

Analysis calculated for C$_{26}$H$_{35}$N$_3$O$_5$S: Requires: C62.25, H7.04, N8.38. Found: C62.43, H7.09, N8.37.

delta$_H$ (250 MHz, D$_6$-DMSO) 8.83 (1H, s, J=1.5 Hz, NHO$\underline{H}$), 8.28 (1H, d, J=8 Hz, CON$\underline{H}$), 7.83 (1H, d, J=6 Hz, CON$\underline{H}$Me), 7.28–6.86 (9H, m, aromatic H), 4.52 (1H, m, C$\underline{H}$CH$_2$Ph), 3.73 (3H, s, OCH$_3$), 2.91 (1H, dd, J=14,4 Hz, CHC$\underline{H}_2$Ph), 2.75 (1H, dd, J=14,10 Hz, CHC$\underline{H}_2$Ph), 2.57 (3H, d, J=4.5 Hz, NHC$\underline{H}_3$), 2.50–2.34 (2H,m), 2.16–1.99 (2H, m, CH$_2$C$\underline{H}$(CH$_3$)$_2$) 1.36 (2H, m), 0.88 (1H, m, C$\underline{H}_2$CH(CH$_3$)$_2$), 0.80 (3H, d, J=6 Hz, CH(C$\underline{H}_3$)$_2$), and 0.73 (3H, d, J=6 Hz, CH(C$\underline{H}_3$)$_2$).

delta$_C$ (63.9 MHz, D$_6$-DMSO) 172.79, 171.62, 168.39, 138.14, 131.34, 129.19, 128.00, 126.44, 114.59, 55.32, 54.20, 38.68, 25.63, 25.17, 24.26, and 21.70

EXAMPLE 10

[4-(N-Hydroxyamino)-2R-isobutyl-3S-(4-hydroxy-phenylthiomethyl) succinyl]-L-phenylalanine-N-methylamide

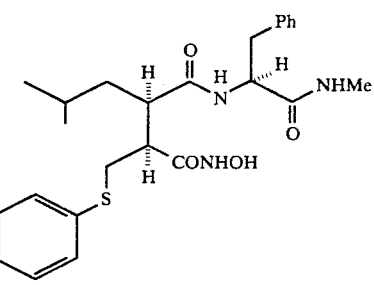

[4-Hydroxy-2R-isobutyl-3S-(4-hydroxyphenylthi-omethyl) succinyl]-L-phenylalanine-N-methylamide (0,4 g, 0.8 mmol) and HOBT (0.15 g, 1.0 mmol) were dissolved in 1:1 DCM/DMF and the mixture cooled to 0° C. before adding WSDCI (0.20 g, 1.0 mmol) and NMM (0.1 g, 1.0 mmol). The mixture was stirred at 0° C. for 1h to ensure complete formation of the activated ester. Hydroxylamine hydrochloride (0.09 g, 1.3 mmol) and NMM (0.13 g,1.3 mmol) were dissolved in DMF then this mixture was added dropwise to the cooled solution of the activated ester. After 1 h the reaction was poured into ether/water (1:1) whereupon the desired product precipitated as white crystals. These were collected by filtration, further washed with ether and water, then dried under vacuum at 50° C. This material was recrystallised from methanol/water (1:1) to remove a trace of the minor diastereomer (0.13 g, 0.2 mmol, 31%).

m.p. 216° C.

[alpha]$_D$= −65° (c=0.5, methanol).

Analysis calculated for C$_{25}$H$_{33}$N$_3$O$_5$S: Requires: C61.58, H6.82, N8.62. Found: C61.43, H6.81, N8.08.

delta$_H$ (250 MHz, D$_6$-DMSO) 8.82 (1H, s, J=1.5 Hz, NHO$\underline{H}$), 8.26 (1H, d, J=8 Hz, CON$\underline{H}$), 7.81 (1H, d, J=6 Hz, CON$\underline{H}$Me), 7.27–6.64 (9H, m, aromatic H), 4.49 (1H, m, C$\underline{H}$CH$_2$Ph), 2.90 (1H, dd, J=14,4 Hz, CHC$\underline{H}_2$Ph), 2.74 (1H, dd, J=14,10 Hz, CHC$\underline{H}_2$Ph), 2.57 (3H, d, J 4.5 Hz, NHC$\underline{H}_3$), 2.54–2.29 (2H, m), 2.14–1.98 (2H, m, CH$_2$C$\underline{H}$(CH$_3$)$_2$), 1.35 (2H, m), 0.88 (1H, m, C$\underline{H}_2$CH(CH$_3$)$_2$), 0.80 (3H, d, J=6 Hz, CH(C$\underline{H}_3$)$_2$), and 0.73 (3H, d, J=6 Hz, CH(C$\underline{H}_3$)$_2$).

delta$_C$ (63.9 MHz, D$_6$-DMSO) 172.81, 171.66, 168.46, 156.50, 133.02, 132.17, 129.17, 128.02, 126.44, 124.17, 116.00, 54.20, 46.35, 46.13, 37.59, 35.40, 25.62, 25.16, 24.27, and 21.69.

EXAMPLE 11

[4-(N-Hydroxyamino)-2R-isobutyl-3S-(2-thienylthiomethyl)succinyl]-L-phenylalanine-N-methylamide sodium salt

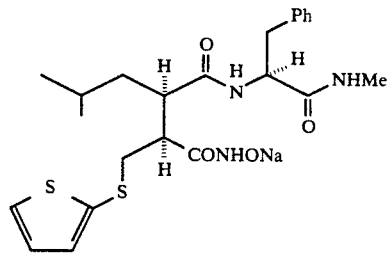

[4-Hydroxyamino)-2R-isobutyl-3S-(2-thienylthiomethyl) succinyl]-L-phenylalanine-N-methylamide (0,2 g, 0.4 mmol) was dissolved in 20 ml of methanol and 1 eq of 0.1N NaOH(aq) added. The solvent was removed in vacuo and the residue dissolved in water and freeze-dried (0.21 g, 0.4 mmol, 100%).

m.p. 170° C.

[alpha]$_D$ = −67° (c=1, methanol).

delta$_H$ (250 MHz, d$_6$-DMSO), 7.51 (1H, d), 7.19–6.97 (8H, m, aromatic H), 4.32 (1H, m, CHCH$_2$Ph), 3.00 (1H, dd, J=14,4 Hz, CHCH$_2$Ph), 2.84 (1H, dd, J=14,10 Hz, CHCH$_2$Ph) 2.53 (3H, d, J=4.5 Hz, NHCH$_3$), 2.46 2.19 (3H, m), 1.37 (1H, m), 1.09 (1H, m), 0.93 (1H, m), and 0.67 (6H, m)

EXAMPLE 12

4-(N-Hydroxyamino)-2R-isobutyl-3S-(4-methoxyphenylthiomethyl)succinyl]-L-phenylalanine-N-methylamide sodium salt

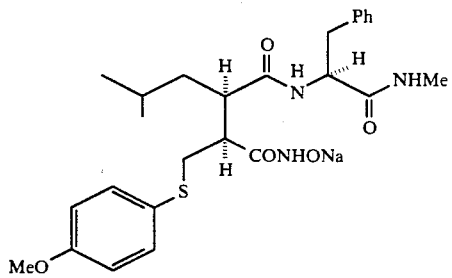

[4-Hydroxyamino)-2R-isobutyl-3S-(4-methoxyphenylthiomethyl)succinyl]-L-phenylalanine-N-methylamide (0,1 g, 0.2 mmol) was dissolved in 20 ml of methanol and 1 eq of 0.1N NaOH(aq) added. The solvent was removed in vacuo and the residue dissolved in water and freeze-dried (0.1 g, 0.2 mmol, 100%).

m.p. 174° C.

[alpha]$_D$ = −58° (c=1, methanol).

delta$_H$ (250 MHz, D$_6$-DMSO 7.26–7.04 (10H, m, aromatic H), 4.31 (1H, m, CHCH$_2$Ph), 3.73 (3H, s, OCH$_3$), 3.25–2.72 (2H, m, CHCH$_2$Ph), 2.50 (3H, s, NHCH$_3$), 2.36 (1H, m), 2.15 (1H, m), 1.37 (1H, m), 0.95 (1H, m), and 0.69 (6H, d, CHCH$_2$(CH$_3$)$_2$).

EXAMPLE 13

[4-(N-Hydroxyamino)-2R-isobutyl-3S-(4-tertbutylphenylthiomethyl) succinyl]-L-phenylalanine-N-methylamide

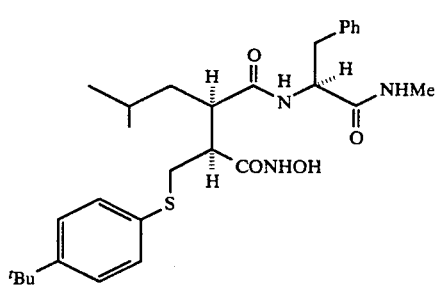

[4-Hydroxy-2R-isobutyl-3S-(4-tertbutylphenylthiomethyl) succinyl]-L-phenylalanine-N-methylamide (5.0 g, 10 mmol) and HOBT (1.76 g, 12 mmol) were dissolved in 1:1 DCM/DMF and the mixture cooled to 0° C. before adding WSDCI (2.3 g, 12 mmol) and NMM (1.2 g, 12 mmol). The mixture was stirred at 0° C. for 1 h to ensure complete formation of the activated ester. Hydroxylamine hydrochloride (1.0 g, 15 mmol) and NMM (1.2 g, 15 mmol) were dissolved in DMF then this mixture was added dropwise to the cooled solution of the activated ester. After 1h the reaction was poured into ether/water (1:1) whereupon the desired product precipitated as white crystals. These were collected by filtration, further washed with ether and water, then dried under vacuum at 50° C. This material was repeatedly recrystallised from methanol/water (1:1) to remove a trace of the minor diastereomer (0.7 g, 1.3 mmol, 14%).

M.p. 188.5°–190° C.

Analysis calculated for C$_{29}$H$_{41}$N$_3$O$_4$S: Requires: C66.00, H7.83, N7.96. Found: C65.80, H7.81, N7.76.

delta$_H$ (250 MHz, D$_6$-DMSO) 8.83 (1H, s, NHOH), 8.33 (1H, d, J=8 Hz, CONH), 7.86 (1H, d, J=6 Hz, CONHMe), 7.28–6.90 (9H, m, aromatic H), 4.60 (1H, m, CHCH$_2$Ph), 2.94 (1H, dd, J=14,4 Hz, CHCH$_2$Ph), 2.77 (1H, dd, J=14,10 Hz, CHCH$_2$Ph), 2.58 (3H, d, J=4.5 Hz, NHCH$_3$), 2.55–2.37 (2H, m), 2.22–2.08 (2H, m, CH$_2$CH(CH$_3$)$_2$), 1.37 (2H, m), 1.26 (9H, s, C(CH$_3$)$_3$), 0.88 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

delta$_C$ (63.9 MHz, D$_6$-DMSO) 172.88, 171.59, 168.34, 147.87, 138.10, 133.09, 129.13, 127.95, 127.45, 126.36, 125.70, 54.19, 54.20, 46.38, 46.06, 37.70, 34.20, 32.79 31.24, 25.64, 25.19, 24.25, and 21.72.

EXAMPLE 14

[4-( N-Hydroxyamino)-2R-isobutyl-3S-(2,4-dimethylphenylthiomethyl) succinyl]-L-phenylalanine-N-methylamide

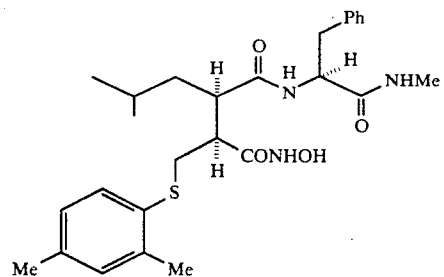

4-Hydroxy-2R-isobutyl-3S-(2,4-dimethylphenylthiomethyl)succinyl]-L-phenylalanine-N-methylamide (1.8 g, 3.7 mmol) and HOBT (0.67 g, 12 mmol) were dissolved in 1:1 DCM/DMF and the mixture cooled to 0° C. before adding WSDCI (0.86 g, 4.5 mmol) and NMM (0.45 g, 4.5 mmol). The mixture was stirred at 0° C. for 1h to ensure complete formation of the activated ester. Hydroxylamine hydrochloride (0.39 g, 5.6 mmol) and NMM (0.56 g, 5.6 mmol) were dissolved in DMF then this mixture was added dropwise to the cooled solution of the activated ester. After 1 h the reaction was poured into ether/water (1:1) whereupon the desired product precipitated as white crystals. These were collected by filtration, further washed with ether and water, then dried under vacuum at 50° C. This material was repeatedly recrystallised from methanol/water (1:1) to remove a trace of the minor diastereomer (1.08 g, 2.2 mmol, 58%).

m.p 226° C. (dec.).

Analysis calculated for $C_{27}H_{37}N_3O_4S$: Requires: C64.90, H7.46, N8.41. Found C65.15, H7.48, N8.40.

delta$_H$ (250 MHz, D$_6$-DMSO) 8.83 (1H, s, NHOH), 8.32 (1H, d, J=8 Hz, CONH), 7.85 (1H, d, J=6 Hz, CONHMe), 7.30-6.71 (9H, m, aromatic H), 4.56 (1H, m, CHCH$_2$Ph), 2.91 (1H, dd, J=14,4 Hz, CHCH$_2$Ph), 2.76 (1H, dd, J=14,10 Hz, CHCH$_2$Ph), 2.57 (3H, d, J=4.5 Hz, NHCH$_3$), 2.53-2.38 (2H, m), 2.23 (3H, s, C$_6$H$_5$(CH$_3$)2), 2.13 (3H, s, C$_6$H$_5$(CH$_3$), 1.30 (2H, m), 0.89 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

EXAMPLE 15

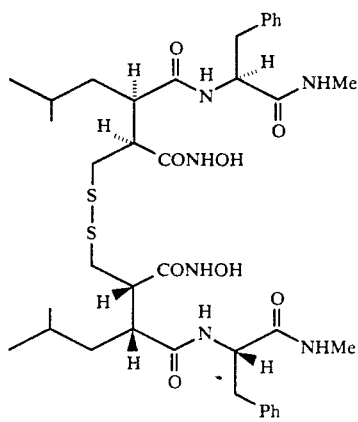

[4(N-Hydroxyamino-2R-isobutyl-3S-(acetylthiomethyl) succinyl]-L-phenylalanine-N-methylamide (1.0 g, 2.4 mmol) was dissolved in 750 ml methanol and 350 ml pH 7 buffer added. Left to stand overnight and solvent removed in vacuo to ⅔ volume, left to crystallise for a further two hours. Filtered and dried to give 0.87 g off-white crystals Analysis calculated for $C_{38}H_{56}N_6O_8S_2.1.9H2O$: Requires: C55.34, H6.93, N9.88, Found: C55.44, H7.32, N10.21.

EXAMPLE 16

[4-(N-Hydroxyamino)-2R-isobutyl-3S-(3-bromophenylthiomethyl) succinyl]-L-phenylalanine-N-methylamide Prepared by the method described in example 1g to give material with the following characteristics.

m.p. 225°-229° C.

[alpha]$_D$= −164.8°.

Analysis calculated for $C_2{}^5H_{32}BrN_3O_4S$: Requires: C54.40, H5.89, N7.40. Found: C54.54, H5.86, N7.63.

delta $_H$ (250 MHz, D$_6$-DMSO) 8.83 (1H, s, NHOH), 8.35 (1H, d, J=8 Hz, COHH), 7.90 (1H, q, J=6 Hz, CONHMe), 7.35-6.87 (9H, m, aromatic H), 4.64 (1H, m, CHCH$_2$Ph), 2.94 (1H, dd, J=14,4 Hz, CHCH$_2$Ph), 2.76 (1H, t, J=13 Hz, CHCH$_2$Ph) 2.60 (3H, d, J=5 Hz, NHCH$_3$), 2.55-2.35 (2H, m, CH$_2$S), 2.15 (1H, t, J=10 Hz, CHCO), 2.01 (1H, d, J=11.5 Hz, CHCO), 1.37 (2H, m), 0.88 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

delta$_C$ (63.9 MHz, D$_6$-DMSO) 173.0, 171.0, 168.8, 139.8, 138.0, 130.5, 129.0, 128.5, 127.5, 125.8, 125.5, 54.2, 46.0, 45.5, 38.0, 31.5, 25.5, 25.2, 24.7, and 21.0.

EXAMPLE 17

[4-(N-Hydroxyamino)-2R-isobutyl-3S-(3-chlorophenylthiomethyl) succinyl]-L-phenylalanine-N-methylamide

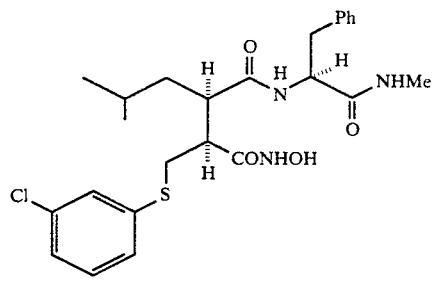

Prepared by the method described in example 1g to give material with the following characteristics.

m.p. 231°-234° C.

[alpha]$_D$= −96.5°.

Analysis calculated for $C_2{}^5H_{32}ClN_3O_4S$. Requires: C59.34, H6.37, N8.30. Found: C59.51, H6.43, N8.24.

delta$_H$ (250 MHz, D$_6$-DMSO) 8.85 (1H, s, NHOH), 8.37 (1H, d, J=8.5 Hz, CONH), 7.90 (1H, m, CONHMe), 7.30-6.88 (9H, m, aromatic H), 4.66 (1H, m, CHCH$_2$Ph), 2.96 (1H, bd, J=14 Hz, CHCH$_2$Ph), 2.76 (1H, bt, J=13 Hz, CHCH$_2$Ph) 2.60 (3H, d, J=5 Hz, NHCH$_3$), 2.55-2.40 (2H, m, CH$_2$S), 2.16 (1H, m, CHCO), 2.01 (1H, d, J=14 Hz, CHCO), 1.37 (2H, m), 0.91 (1H, m, CH$_2$CH(CH$_3$)$_2$), 0.81 (3H, d, J=6 Hz, CH(CH$_3$)$_2$), and 0.74 (3H, d, J=6 Hz,CH(CH$_3$)$_2$).

delta$_C$ (63.9 MHz, D$_6$-DMSO) 172.7, 171.6, 168.1, 139.2, 138.1, 130.3, 129.2, 127.9, 126.2, 125.9, 125.5, 125.0, 54.1, 46.3, 45.8, 37.8, 32.0, 25.7, 25.2, 24.2, and 21.7.

EXAMPLE 18

[4-(N-Hydroxyamino)-2R-isobutyl-3S-(3-methyl-phenylthiomethyl)succinyl]-L-phenylalanine-N-methylamide

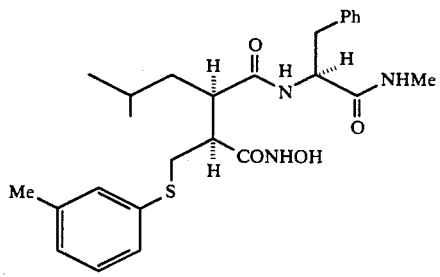

Prepared by the method described in example 1g to give material with the following characteristics.

Analysis calculated for $C_{26}H_{35}N_3O_4S$: Requires: C64.30, H7.26, N8.65. Found: C63.81, H7.21, N8.48.

$delta_H$ (250 MHz, $D_6$-DMSO) 8.83 (1H, s, NHOH), 8.35 (1H, d, J=8.5 Hz, CONH), 7.86 (1H, m, CONHMe), 7.28–6.77 (9H, m, aromatic H), 4.66 (1H, m, CHCH$_2$Ph), 2.96 (1H, dd, J=14,4 Hz, CHCH$_2$Ph), 2.80 (1H, bt, J=13 Hz, CHCH$_2$Ph) 2.59 (3H, d, J=5 Hz, NHCH$_3$), 2.55–2.37 (2H, m, CH$_2$S), 2.16 (2H, m, 2xCHCO), 1.38 (2H, m), 0.91 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

EXAMPLE 19

[4-(N-Hydroxyamino)-2R-isobutyl-3S-(4-(N-acetyl)aminophenylthiomethyl)succinyl]-L-phenylalanine-N-methylamide.

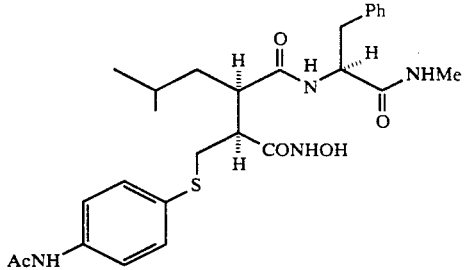

A)
[2R-isobutyl-3S-(4-aminophenylthiomethyl)succinyl]-L-phenylalanine-N-methylamide Prepared by the method described in example 1f to give material with the following characteristics.

$delta_H$ (250 MHz, $D_6$-DMSO) 8.27 (1H, d, J=8.5 Hz, CONH), 7.81 (1H, m, CONHMe), 7.30–7.00 (5H, m, phenyl H), 6.86 (2H, d, J=8.5 Hz, aromatic H), 6.45 (2H, d, J=8.5 Hz, aromatic H), 5.25 (1H, bs, CO$_2$H), 4.48 (1H, m, CHCH$_2$Ph), 2.91 (1H, dd, J=14,4 Hz, CHCH$_2$Ph), 2.88 (1H, dd, J=14,10 Hz, CHCH$_2$Ph) 2.56 (3H, d, J=5 Hz, NHCH$_3$), 2.43–2.24 (3H, m, CH$_2$S and CHCO), 2.03 (1H, d, J=10 Hz, CHCO), 1.41 (1H, t, J=11 Hz, CH$_2$CH(CH$_3$)$_2$), 1.26 (1H, m, CH$_2$CH(CH$_3$)$_2$), 0.85 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

B) [2R-isobutyl-3S (4-(N-acetyl)aminophenyl-thiomethyl)-succinyl]-L-phenylalanine-N-methylamide The product from above (350 mg, 0.74 mmol) was dissolved in DCM (5 ml) cooled in an ice bath then triethylamine (75 mg, 0.74 mmol), DMAP (91 mg, 7.4 mmol) and finally acetic anhydride (83 mg, 8.2 mmol) were added and the solution stirred at RT for 90 minutes. The mixture was partitioned between ethyl acetate and citric acid then the organic layer washed with water and finally dried over magnesium sulphate. Solvent removal gave the crude product as pale yellow crystals (160 mg, 0.31 mmol, 42%).

$delta_H$ (250 MHz, $D_6$-DMSO) 9.94 (1H, s, CO$_2$H), 8.34 (1H, d, J=8.5 Hz, CONH), 7.90 (1H, m, CONHMe), 7.46 (2H, d, J=8.5 Hz, aromatic H) 7.30–7.00 (5H, m, phenyl H), 6.96 (2H, d, J=8.5 Hz, aromatic H), 4.57 (1H, m, CHCH$_2$Ph), 2.91 (1H, dd, J=14,4 Hz, CHCH$_2$Ph), 2.88 (1H, bt, J=13 Hz, CHCH$_2$Ph), 2.58 (3H, d, J=5 Hz, NHCH$_3$), 2.43–2.16 (3H, m, CH$_2$S and CHCO), 2.10 (1H, d, J=14 Hz, CHCO), 1.35 (1H, t, J=14 Hz, CH$_2$CH(CH$_3$)$_2$), 1.26 (1H, m, CH$_2$CH(CH$_3$)$_2$), 0.86 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

C)
[4-(N-Hydroxyamino)-2R-isobutyl-3S-(4-(N-acetyl)aminophenylthiomethyl)succinyl]-L-phenylalanine-N-methylamide Prepared by the method described in example 1g to give material with the following characteristics.

m.p. 201°–202° C. (dec.).

$[alpha]_D = -7.5°$ (c=1.0, methanol).

$delta_H$ (250 MHz, $D_6$-DMSO) 9.90 (1H, s, NHOH), 8.82 (1H, s, NHOH), 8.30 (1H, d, J=8.5 Hz, CONH), 7.85 (1H, m, CONHMe), 7.45 (2H, d, J=8.5 Hz, aromatic H), 7.28–6.94 (5H, m, phenyl H), 6.90 (2H, d, J=8.5 Hz, aromatic H), 4.66 (1H, m, CHCH$_2$Ph), 2.90 (1H, dd, J=14,4 Hz, CHCH$_2$Ph), 2.76 (1H, bt, J=13 Hz, CHCH$_2$Ph), 2.50 (3H, d, J=5 Hz, NHCH$_3$), 2.49–2.35 (2H, m, CH$_2$S), 2.14 (1H, m, CHCO), 2.03 (4H, s+m, COCH$_3$ and CHCO), 1.35 (2H, m), 0.86 (1H, m, CH$_2$CH(CH$_3$)$_2$), 0.81 (3H, d, J=6 Hz, CH(CH$_3$)$_2$), and 0.74 (3H, d, J=6 Hz, CH(CH$_3$)$_2$).

EXAMPLE 20

[4-(N-Hydroxyamino)-2R-isobutyl-3S-phenylsulfinyl-methylsuccinyl]-L-phenylalanine-N-methylamide.

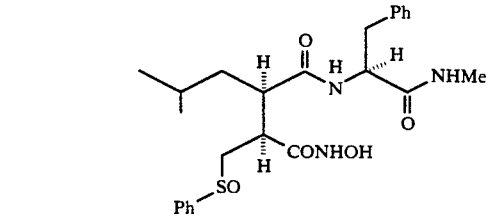

[4-(N-Hydroxyamino)-2R-isobutyl-3S-phenylthiomethylsuccinyl]-L-phenylalanine-N-methylamide (250 mg, 0.53 mmol) was dissolved in methanol (50 ml) and meta-chloroperbenzoic acid (100 mg, 0.58 mmol) was added. After stirring for 1h at room temperature ether was added and the mixture filtered. Solvent removal gave the crude white solid which was recrystallised from methanol / water then slurried in ether to remove final traces of meta-chlorobenzoic acid to give the desired material (70 mg, 0.014 mmol, 27%).

m.p. 186°-188° C.

[alpha]$_D$= −13.6° (c=0.5, methanol).

Analysis calculated for C$_{25}$H$_{33}$N$_3$O$_5$S.0.5H$_2$O: Requires: C60.46, H6.90, N8.46. Found: C60.58, H6.69, N8.29.

delta$_H$ (250 MHz, D$_6$-DMSO, mixture of diastereomers) 9.04 +8.93 (1H, 2xs, NHOH), 8.29+8.16 (1H, 2xd, J=8.5 Hz, CONH), 7.79 (1H, m, CONHMe), 7.90-7.40 (8H, m, aromatic H), 7.06+6.82 (2H, 2xm, SO-Aromatic), 4.37 (1H, m, CHCH$_2$Ph), 2.93-2.58 (3H, m, containing CHCH$_2$Ph), 2.52 (3H, m, NHCH$_3$), 2.49+2.37 (1H, 2xm), 1.49-1.25 (2H, m, CH$_2$CH(CH$_3$)$_2$ and CH2CH(CH$_3$)$_2$), 0.95 (1H, m, CH$_2$CH(CH$_3$)$_2$ ), 0.81 (3H, d, J=6 Hz, CH(CH$_3$)$_2$), and 0.74 (3H, d, J=6 Hz, CH(CH$_3$)$_2$).

delta$_C$ (63.9 MHz, D$_6$-DMSO, mixture of diastereomers) 172.2, 171.4, 171.3, 167.7, 144.5, 138.0, 137.9, 131.3, 130.9, 129.6, 129.3, 129.1, 128.8, 128.3, 127.8, 126.5, 126.2, 124.3, 123.6, 59.8, 58.1, 54.3, 54.0, 46.2, 45.8, 41.6, 40.9, 37.6, 37.4, 25.6, 25.0, 24.3, 24.2, 21.7, and 21.6.

EXAMPLE 21

[4-(N-Hydroxyamino)-2R-isobutyl-3S-phenylsulfonyl-methylsuccinyl]-L-phenylalanine-N-methylamide.

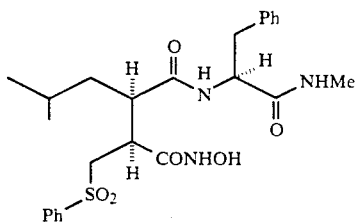

[4-(N-Hydroxyamino)-2R-isobutyl-3S-phenylthiomethylsuccinyl]-L-phenylalanine-N-methylamide (50 mg, 0.11 mmol) was dissolved in methanol (12 ml) and meta-chloroperbenzoic acid (40 mg, 0.23 mmol) was added. After stirring for 3 h at room temperature ether was added and the mixture filtered. Solvent removal gave the crude white solid which was slurried in ether to remove final traces of meta-chlorobenoic acid to give the desired material.

m.p. 228°-231° C.

[alpha]$_D$=16.8° (c=0.5, methanol).

Analysis calculated for C$_{25}$H$_{33}$N$_3$O$_6$S.0.3H$_2$O: Requires: C58.99, H6.65, N8.25. Found: C58.92, H6.51, N8.05.

delta$_H$ (250 MHz, D$_6$-DMSO) 8.66 (1H, s, NHOH), 8.25 (1H, d, J=8.5 Hz, CONH), 7.83 (1H, m, CONHMe), 7.75-7.50 (5H, m, aromatic H), 7.30 7.05 (5H, m, aromatic H), 4.36 (1H, m, CHCH$_2$Ph), 2.S6 (1H, dd, J 14,5 Hz, CHCH$_2$Ph), 2.75 (1H, dd, J=14,10 Hz, CHCH$_2$Ph), 2.54 (3H, d, J=4.5 Hz, NHCH$_3$), 2.54 (2H, m), 1.30 (2H, m, CH$_2$CH(CH$_3$)$_2$ and CH$_2$CH(CH$_3$)$_2$), 0.86 (1H, m, CH$_2$CH(CH$_3$)$_2$), 0.75 (3H, d, J=6 Hz, CH(CH$_3$)$_2$), and 0.71 (3H, d, J=6 Hz, CH(CH$_3$)$_2$).

EXAMPLE 22

[4-(N-Hydroxyamino)-2R-isobutyl-3S-2-thienylsulphinylmethylsuccinyl]-L-phenylalanine-N-methylamide

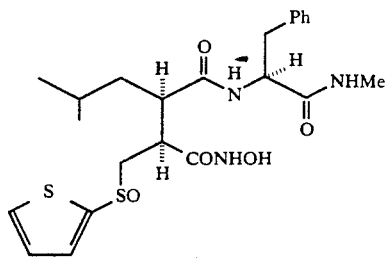

[4-(N-Hydroxyamino)-2R-isobutyl-3S-thienylthiomethyl-succinyl]-L-phenylalanine-N-methylamide (50 mg, 0.11 mmol) was treated as described in Example 21 to yield the title compound (16 mg, 0.03 mmol, 29%) as a mixture of diastereomer with the following characteristics:

m.p. 195°-197° C. (dec.).

Analysis calculated for C$_{23}$H$_{31}$N$_3$O$_5$S$_2$.0.5H$_2$O: Requires: C54.96, H6.42, N8.36. Found: C54.91, H6.23, N8.23.

delta$_H$ (250 MHz, D$_6$-DMSO, mixture of diastereomers) 9.04+8.96 (1H, 2xs, NHOH), 8.34+8.29 (1H, 2xd, J=8.5 Hz, CONH), 8.02+7.98 (1H, 2xm, CONHMe), 7.8I (1H, bs, thiophene-H), 7.42 (1H, s, thiophene-H), 7.25-7.15 (5H, m, phenyl), 7.03 (1H, bs, thiophene-H), 4.43 (1H, m, CHCH$_2$Ph), 3.0-2.6 (4H, m, containing CHCH$_2$Ph), 2.52 (7H, m, containing NHCH$_3$), 2.05 (1H, m), 1.6-1.2 (2H, m, CH$_2$CH(CH$_3$)$_2$ and CH$_2$CH(CH$_3$)$_2$), 0.87 (1H, m, CH$_2$CH(CH$_3$)$_2$), and 0.85-0.71 (6H, m, CH(CH$_3$)$_2$).

EXAMPLE 23

[4-(N-Hydroxyamino)-2R-isobutyl-3S-2-thienylsulphonylmethyl-succinyl]-L-phenylalanine-N-methylamide.

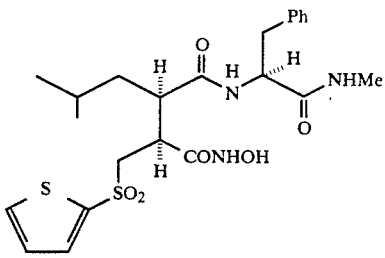

[4-(N-Hydroxyamino)-2R-isobutyl-3S-thiophenylthiomethyl-succinyl]-L-phenylalanine-N-methylamide (75 mg, 0.16 mmol) was treated as described in example 22 to yield the title compound (40 mg, 0.08 mmol, 49%) with the following characteristics:

m p. 215°-216° C.

Analysis calculated for C$_{23}$H$_{31}$N$_3$O$_6$S$_2$: Requires: C54.21, H6.13, N8.24. Found C54.07, H6.19, N8.04.

delta$_H$ (250 MHz, D$_6$-DMSO) 887 (1H, s, NHOH), 8.25 (1H, d, J=8.5 Hz, CONH), 8.09 (1H, d, J=4.7 Hz, thiophene-H), 7.83 (1H, m, CONHMe), 7.53 (1H, d, J=3 Hz, thiophene H), 7.25-7.12 (6H, m, phenyl and thiophene-H), 4.36 (1H, m, CHCH$_2$Ph), 3.38 (1H, dd, J=14,11 Hz, SCH$_2$), 2.87 (1H, dd, J=14,5 Hz, CHCH2Ph), 2.75 (1H, dd, J=14,10 Hz, CHCH2Ph), 2.70-2.36 (6H, m, containing NHCH3), 1.20 (2H, m, CH2CH(CH3)2 and CH2CH(CH3)2), 0.89 (1H,m, CH2CH(CH3)2 ), and 0 75 (6H, m, CH(CH3)2).

delta$_C$ (63.9 MHz, D6-DMSO) 172.0, 171.2, 166.5, 140.0, 138.0, 135.4, 134.6, 129.0, 128.4, 128.2, 126.6, 54.3, 45.6, 37.5, 25.6, 25.0, 24.2, and 21.7.

EXAMPLE 24

[4-(N-Hydroxyamino)-2R-isobutyl-3S-phenylsulfonyl-methylsuccinyl]-L-phenylalanine-N-methylamide sodium salt

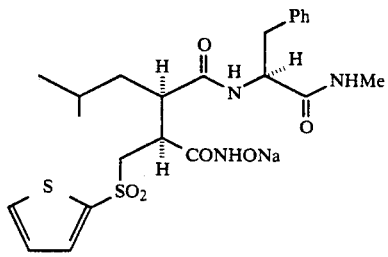

[4-(N-Hydroxyamino)-2R-isobutyl-3 S-phenylsulfonylmethylsuccinyl]-L-phenylalanine-N-methylamide (50 mg, 0.1 mmol) was dissolved in methanol (10 ml) and sodium hydroxide solution (0.1M, 1.0 ml) added to give a homogeneous solution. The methanol was removed under reduced pressure then the residual aqueous solution freeze dried to give the title compound (40 mg).

delta$_H$ (250 MHz, D6-DMSO) 8.66 (1H, s, NHOH), 8.25 (1H, d, J=8.5 Hz, CONH), 7.83 (1H, m, CONHMe), 7.75-7.50 (5H, m, aromatic H), 7.30 7.05 (5H, m, aromatic H), 4.36 (1H, m, CHCH2Ph), 2.86 (1H, dd, J=14,5 Hz, CHCH2Ph), 2.75 (1H, dd, J=14,10 Hz, CHCH2Ph), 2.54 (3H, d, J=4.5 Hz, NHCH3), 2.54 (2H, m), 1.30 (2H, m, CH2CH(CH3)2 and CH2CH(CH3)2), 0.86 (1 H, m, CH2CH(CH3)2), 0.75 (3H, d, J=6 Hz, CH(CH3)2), and 0.71 (3H, d, J=6 Hz, CH(CH3)2).

EXAMPLE 25

[4-(N-Hydroxyamino)-2R-isobutyl-3S-(4-(isobutyloxycarbonylamino)phenyl)thiomethyl-succinyl]-L-phenylalanine-N-methylamide

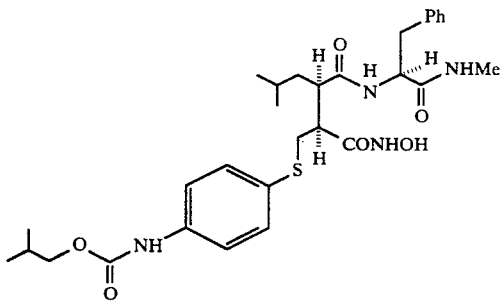

a) [4-Hydroxy-2R-isobutyl-3S-(4-aminophenyl)thiomethylsuccinyl] -L-phenylalanine-N-methylamide was prepared by the method described in example 1f to give a compound with the following characteristics.

delta$_H$(250 MHz, D6-DMSO) 8.26 (1H, d, J=8.5 Hz, CONH), 7.81 (1H, m, CONHMe), 7.27-7.15 (5H, m, phenyl H), 6.85 (2H, d, J=8.5 Hz, aromatic H), 6.46 (2H, d, J=8.5 Hz, aromatic H), 5.2 (1H, bs, CO2H), 4.48 (1H, m, CHCH2Ph), 2.90 (1H, dd, J=13.5,4.3 Hz, CHCH2Ph), 2.75 (1H, dd, J=13.6, 10 Hz, CHCH2Ph), 2.56 (3H, d, J=4.5 Hz, NHCH3), 2.50-2.25 (3H, m), 2.03 (1H, d, J=10 Hz), 1.41 (1H, m, CH2CH(CH3)2), 1.26 (1H, m, CH2CH(CH3)2), 0.86 (1H, m, CH2CH(CH3)2), 0.75 (3H, d, J =6 Hz, CH(CH3)2), and 0.71 (3H, d, J=6 Hz,CH(CH3)2).

b) N,N-Dimethylglycine (100 mg, 0.97 mmol) was stirred in dry THF (50 ml) and triethylamine (108 mg, 1.1 mmol) and isobutylchloroformate (146 mg, 1.1 mmol) were added. After 1 h the product from example 26a (500 mg, 1.1 mmol) was addedand the mixture stirred for a further 1 h. The reaction was worked up by partitioning between citric acid and ethyl acetate, drying the organic layer and solvent removal to give the crude product (1 g) Solution of the crude solid in ethyl acetate then precipitation with ether resulted in white crystals of the isobutylchloroformate derivative.

c) [4-(N-Hydroxyamino)-2R-isobutyl-3S-(4-(isobutyloxycarbonylamino) phenyl)thiomethyl-succinyl]-L-phenylalanine-N-methylamide The product from example 26b was converted to the hydroxamic acid as described in example 1g to give a compound with the following characteristics.

m.p. 198°-200° C.

[alpha]$_D$=−8.5° (c=1, methanol).

Analysis calculated for C30H42N4O6S: Requires: C61.41, H7.22, N9.55. Found: C62.04, H7.32, N9.67.

delta$_H$ (250 MHz, D6-DMSO) 9.60 (1H, s, NHOH), 8.83 (1H, s, NHOH), 8.31 (1H, d, J=8.5 Hz, CONH), 7.85 (1H, m, CONHMe), 7.36-7.25 (4H, m, aromatic H), 7.14-7.05 (3H, m, aromatic H), 6.91 (2H, d, J=8.5 Hz, aromatic H), 4.56 (1H, m, CHCH2Ph), 3.87 (2H, d, J=7 Hz, OCH2CH(CH3)2), 2.92 (1H, dd, J=13.7,4.0 Hz, CHCH2Ph), 2.76 (1H, dd, J=13.6,10 Hz, CHCH2Ph), 2.58 (3H, d, J =4.5 Hz, NHCH3), 2.50-2.34 (2H, m), 2.16-1.87 (3H, m), 1.35 (2H, m, CH2CH(CH3)2 and CH2CH(CH3)2), 0.93 (6H, d, J=6.6 Hz, OCH2CH(CH3)2), 0.87 (1H,m, CH2CH(CH3)2), 0.75 (3H, d, J=6 Hz, CH(CH3)2), and 0.71 (3H, d, J=6 Hz, CH(CH3)2).

EXAMPLE 26

[4-(N-Hydroxyamino)-2R-isobutyl-3S-(4-(N-methyl-N-(tertbutoxycarbonyl)-glycylamino) phenyl)thiomethylsuccinyl]-L-phenylalanine-N-methylamide.

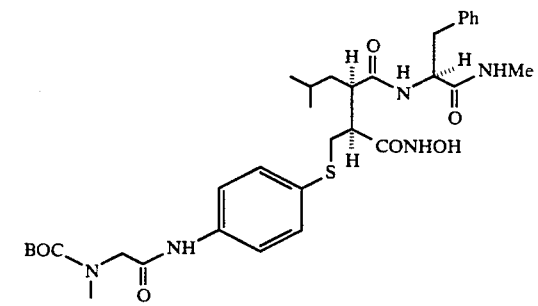

a) [4-Hydroxy-2R-isobutyl-3S-(4-(N-methyl-N-(tert-butoxycarbonyl)glycylamino) phenyl)thiomethylsuccinyl]-L-phenylalanine-N-methylamide was prepared as described in example 26b by substitution of N-BOC sarcosine for the acid component.

delta$_H$ (250 MHz, D$_6$-DMSO) 9.97 (1H, s, CO$_2$H̄), 8.36 (1H, d, J=8.5 Hz, CONH̄), 7.91 (1H, m, CONH̄Me), 7.48 (2H, d, J=8.5 Hz, aromatic H), 7.40–7.05 (5H, m, aromatic H), 6.97 (2H, d, J=8.5 Hz, aromatic H), 4.58 (1H, m, CH̄CH$_2$Ph), 3.95 (2H, d, J=9 Hz, NCH̄$_2$CO), 2.92 (4H̄, m+d, CHCH̄$_2$Ph and BOCNCH̄$_3$), 2.76 (1H, dd, J=13,10 Hz, CH̄CH$_2$Ph), 2.58 (3H̄, d, J=4.5 Hz, NHCH$_3$), 2.50–2.09 (4H̄, m), 1.46–1.33 (11H, m+2xs, (CH$_3$)$_3$C, CH$_2$CH(CH$_3$)$_2$ and CH$_2$CH(CH$_3$)$_2$), 0.87 (1H, m, CH$_2$CH̄(CH$_3$)$_2$), 0.75 (3H, d, J=6 Hz, CH(CH̄$_3$)$_2$), and 0.71 (3H, d, J=6 Hz, CH(CH̄$_3$)$_2$).

b) [4̄-(N-Hydroxyamino)-2R-isobutyl-3S-(4-(N-methyl-N-(tertbutoxycarbonyl)-glycylamino)phenyl)-thiomethylsuccinyl]-L-phenylalanine-N-methylamide was prepared from the material produced in example 27a as described in example 1g.

delta$_H$ (250 MHz, D$_6$-DMSO) 9.97 (1H, s, CONHOH̄), 8.83 (1H, s, NHOH̄), 8.32 (1H, d, J=8.5 Hz, CONH̄), 7.86 (1H, m, CONH̄Me), 7.46 (2H, d, J=8.5 Hz, aromatic H), 7.28–7.00 (5H, m, aromatic H), 6.97 (2H, d, J=8.5 Hz, aromatic H), 4.56 (1H,, m, CH̄CH$_2$Ph), 3.94 (2H, d, J=9 Hz, NCH̄$_2$CO), 2.87 (4H, m+d, CHCH̄$_2$Ph and BOCNCH̄$_3$), 2.76 (1H, m, CH̄CH$_2$Ph), 2.57 (3H, d, J=4.5 Hz, NHCH̄$_3$), 2.25–1.91 (2H, m), 1.42–1.30 (11H, m+2xs, (CH$_3$)$_3$C, CH$_2$CH(CH$_3$)$_2$ and CH$_2$CH(CH$_3$)$_2$), 0.92 (1H̄, m, CH̄$_2$CH(CH$_3$)$_2$), 0.80 (3H, d, J=6 Hz, CH(CH̄$_3$)$_2$), and 0.73 (3H, d, J=6 Hz, CH(CH̄$_3$)$_2$).

EXAMPLE 27

Collagenase inhibition activity

The potency of compounds of general formula I to act as inhibitors of collagenase (a metalloprotease involved in tissue degradation) was determined by the procedure of Cawston and Barrett, (*Anal. Biochem*, 99, 340–345, 1979), hereby incorporated by reference, whereby a 1 mM solution of the inhibitor being tested or dilutions thereof was incubated at 37° for 16 hours with collagen and collagenase (buffered with 25 mM Hepes, pH 7.5 containing 5 mM CaCl$_2$, 0.05% Brij 35 and 0.02% NaN$_3$). The collagen was acetylated $^{14}$C collagen prepared by the method of Cawston and, Murphy (*Methods in Enzymology*, 80, 711, 1981), hereby incorporated by reference. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported below as that inhibitor concentration effecting 50% inhibition of the collagenase (IC$_{50}$).

| Compound of Example No. | IC$_{50}$ |
|---|---|
| 1 | 20 nM |
| 2 | 8 nM |
| 5 | 3 nM |
| 6 | (50% @ 1 mcM) |

EXAMPLE 28

Stromelysin inhibition activity

The potency of compounds of general formula I to act as inhibitors of stromelysin was determined using the procedure of Cawston et al (*Biochem. J.*, 195, 159–165 1981), hereby incorporated by reference, whereby a 1 mM solution of the inhibitor being tested or dilutions thereof was incubated at 37° C. for 16 hours with stromelysin and $^{14}$C acetylate casein (buffered with 25 mM Hepes, pH 7.5 containing 5 mM CaCl$_2$, 0.05% Brij 35 and 0.02% NaN$_3$. The casein was $^{14}$C acetylated according to the method described in Cawston et al (*Biochem J.*, 195, 159–165, 1981), hereby incorporated by reference. The stromelysin activity in the presence of 1 mM, or a dilution thereof, was composed to activity in a control devoid of inhibitor and the results reported below as that inhibitor concentration effecting 50% inhibition of the stromelysin (IC$_{50}$).

| Compound of Example No. | IC$_{50}$ |
|---|---|
| 1 | 10 nM |
| 2 | 20 nM |

Examples of unit dosage compositions are as follows:

EXAMPLE 29

Capsules:

| | Ingredients | Per Capsule | Per 10,000 Capsules |
|---|---|---|---|
| 1. | Active ingredient Cpd. of Form. I | 40.0 mg | 400 g |
| 2. | Lactose | 150.0 mg | 1500 g |
| 3. | Magnesium stearate | 4.0 mg | 40 g |
| | | 194.0 mg | 1940 g |

Procedure for capsules

Step 1. Blend ingredients No. 1 and No. 2 in a suitable blender.

Step 2. Pass blend from Step 1 through a No. 30 mesh (0.59 mm) screen.

Step 3. Place screened blend from Step 2 in a suitable blender with ingredient No. 3 and blend until the mixture is lubricated.

Step 4. Fill into No. 1 hard gelatin capsule shells on a capsule machine.

EXAMPLE 30

Tablets:

| | Ingredients | Per Tablet | Per 10,000 Tablets |
|---|---|---|---|
| 1. | Active ingredient Cpd. of Form. I | 40.0 mg | 400 g |
| 2. | Corn Starch | 20.0 mg | 200 g |
| 3. | Alginic acid | 20.0 mg | 200 g |
| 4. | Sodium alginate | 20.0 mg | 200 g |
| 5. | Magnesium stearate | 1.3 mg | 13 g |
| | | 101.3 mg | 1013 g |

Procedure for tablets

Step 1. Blend ingredients No. 1, No. 2, No. 3 and No. 4 in a suitable mixer/blender.

Step 2. Add sufficient water portionwise to the blend from Step 1 with careful mixing after each addition. Such additions of water and mixing until the mass is of a consistency to permit its conversion to wet granules.

Step 3. The wet mass is converted to granules by passing it through an oscillating granulator using a No. 8 mesh (2.38) screen.

Step 4. The wet granules are then dried in an oven at 140° F. (60° C.) until dry.

Step 5. The dry granules are lubricated with ingredient No. 5.

Step 6. The lubricated granules are compressed on a suitable tablet press.

EXAMPLE 11

| Intramuscular Injection: | | |
|---|---|---|
| Ingredient | Per ml. | Per liter |
| 1. Compound of Formula I Active ingredient | 10.0 mg | 10 g |
| 2. Istonic buffer solution pH 4.0. | q.s. | q.s. |

Procedure

Step 1. Dissolve the active ingredient in the buffer solution.

Step 2. Aseptically filter the solution from Step 1.

Step 3. The sterile solution is now aseptically filled into sterile ampoules.

Step 4. The ampoules are sealed under aspetic conditions.

EXAMPLE 32

| Suppositories: | | |
|---|---|---|
| Ingredients | Per Supp. | Per 1,000 Supp |
| 1. Compound of Form. I Active ingredient | 40.0 mg | 40 g |
| 2. Polyethylene Glycol 1000 | 1350.0 mg | 1,350 g |
| 3. Polyethylene Glycol 4000 | 450.0 mg | 450 g |
| | 1840.0 mg | 1,840 g |

Procedure

Step 1. Melt ingredient No. 2 and No. 3 together and stir until uniform.

Step 2. Dissolve ingredient No. 1 in the molten mass from Step 1 and stir until uniform.

Step 3 Pour the molten mass from Step 2 into suppository moulds and chill.

Step 4 Remove the suppositories from moulds and wrap.

EXAMPLE 33

Eye Ointment

An appropriate amount of a compound of general formula I is formulated into an eye ointment base having the following composition:

| Liquid paraffin | 10% |
|---|---|
| Wool fat | 10% |
| Yellow soft paraffin | 80% |

EXAMPLE 34

Topical skin ointment

An appropriate amount of a compound of general formula I is formulated into a topical skin ointment base having the following composition:

| Emulsifying wax | 30% |
|---|---|
| White soft paraffin | 50% |
| Liquid paraffin | 20% |

What is claimed is:

1. A compound of general formula I:

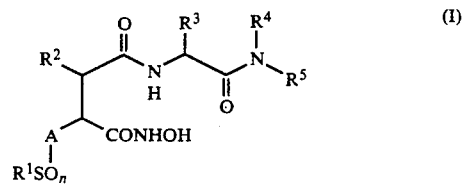

represents thienyl;

$R^2$ represents a hydrogen atom or a $C_1$-$C_6$ alkyl, $C_1$-$C_6$ alkenyl, phenyl($C_1$-$C_6$)alkyl, cycloalkyl($C_1$-$C_6$)alkyl or cycloalkenyl($C_1$-$C_6$)alkyl group;

$R^3$ represents an amino acid side chain or a $C_1$-$C_6$ alkyl, benzyl, ($C_1$-$C_6$alkoxy)benzyl or benzyloxy($C_1$-$C_6$ alkyl) or benzyloxy benzyl group;

$R^4$ represents a hydrogen atom or a $C_1$-$C_6$ alkyl group;

$R^5$ represents a hydrogen atom or a methyl group;

n is an integer having the value 0, 1 or 2; and

A represents a $C_1$-$C_6$ hydrocarbon chain, optionally substituted with one or more $C_1$-$C_6$ alkyl, phenyl or substituted phenyl groups;

or a salt thereof.

2. A compound as claimed in claim 1, in which the chiral center adjacent the substituent $R^3$ has S stereochemistry.

3. A compound as claimed in claim 1, wherein the chiral center adjacent the substituent $R^2$ has R stereochemistry.

4. A compound as claimed in 1, wherein $R^2$ represents a $C_3$-$C_6$ alkyl group.

5. A compound as claimed in claim 1, wherein $R^3$ represents a benzyl or 4-($C_1$-$C_6$)alkoxyphenylmethyl or benzyloxybenzyl group.

6. A compound as claimed in claim 1, wherein $R^4$ represents a $C_1$-$C_4$ alkyl group.

7. A compound as claimed in claim 1, wherein $R^5$ represents a hydrogen atom.

8. A compound according to claim 1, which is selected from the group consisting of:

[4-(N-Hydroxyamino)-2R-isobutyl-3S-(2-thienylthiomethyl) succinyl]-L-phenylalanine-N-methylamide,

[4-(N-Hydroxyamino)-2R-isobutyl-3S-(2-thienylthiomethyl) succinyl]-L-phenylalanine-N-methylamide sodium salt,

[4-(N-Hydroxyamino)-2R-isobutyl-3S-2-thienylsulphinylmethyl-succinyl]-L-phenylalanine-N-methylamide,

[4-(N-Hydroxyamino)-2R-isobutyl-3S-2-thienylsulphonylmethyl-succinyl]-L-phenylalanine-N-methylamide.

9. A compound which is [4-(N-Hydroxyamino)-2R-isobutyl-3S-(2-thienylthiomethyl) succinyl]-L-phenylalanine-N-methylamide or a salt thereof.

10. A pharmaceutical or veterinary formulation comprising a compound as claimed in claim 1 and a pharmaceutically and/or veterinarily acceptable carrier.

11. A pharmaceutical composition comprising a compound of the formula
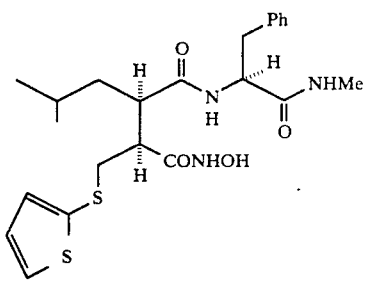
and the pharmaceutically acceptable salts thereof and a pharmaceutically acceptable carrier.
* * * * *

UNITED STATES PATENT AND TRADEMARK OFFICE
CERTIFICATE OF CORRECTION

PATENT NO. : 5,240,958
DATED : August 31, 1993
INVENTOR(S) : Campion et al.

It is certified that error appears in the above-identified patent and that said Letters Patent is hereby corrected as shown below:

In column 34, line 18, insert -- wherein R' -- before "represents thienyl".

Signed and Sealed this

Fourth Day of October, 1994

*Attest:*

BRUCE LEHMAN

*Attesting Officer*     *Commissioner of Patents and Trademarks*